(12) United States Patent
Guckian et al.

(10) Patent No.: US 8,293,923 B2
(45) Date of Patent: Oct. 23, 2012

(54) INDAZOLE DERIVATIVES AS MODULATORS OF INTERLEUKIN-1 RECEPTOR-ASSOCIATED KINASE

(75) Inventors: Kevin Guckian, Marlborough, MA (US); Charles Jewell, Sudbury, MA (US); Patrick Conlon, Wakefield, MA (US); Edward Yin Shiang Lin, Chestnut Hill, MA (US); Timothy Chan, Newton, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 579 days.

(21) Appl. No.: 12/440,163

(22) PCT Filed: Sep. 7, 2007

(86) PCT No.: PCT/US2007/019588
§ 371 (c)(1),
(2), (4) Date: Sep. 3, 2009

(87) PCT Pub. No.: WO2008/030584
PCT Pub. Date: Mar. 13, 2008

(65) Prior Publication Data
US 2011/0152260 A1    Jun. 23, 2011

Related U.S. Application Data

(60) Provisional application No. 60/842,801, filed on Sep. 7, 2006.

(51) Int. Cl.
*A61K 31/4188* (2006.01)
*A61K 31/5355* (2006.01)
*C07D 401/14* (2006.01)
*C07D 403/12* (2006.01)

(52) U.S. Cl. ............. 548/305.1; 514/231.5; 514/253.09; 514/318; 514/338; 514/387; 544/124; 544/364; 546/194; 546/273.4

(58) Field of Classification Search ................ 548/305.1
See application file for complete search history.

(56) References Cited

FOREIGN PATENT DOCUMENTS

| WO | WO-98/43969 A1 * | 10/1998 |
| WO | WO 03/030902 A1 | 4/2003 |
| WO | WO 03/082272 A1 | 10/2003 |

OTHER PUBLICATIONS

Golub et al., Science, vol. 286, Oct. 15, 1999, pp. 531-537.*

* cited by examiner

*Primary Examiner* — Laura L. Stockton
(74) *Attorney, Agent, or Firm* — Steptoe & Johnson LLP

(57) ABSTRACT

The present invention relates to modulators of IRAK kinases of formula (I) and provides compositions comprising such modulators, as well as methods therewith for treating IRAK-mediated or IRAK-associated conditions or diseases.

27 Claims, No Drawings

INDAZOLE DERIVATIVES AS MODULATORS OF INTERLEUKIN-1 RECEPTOR-ASSOCIATED KINASE

CLAIM OF PRIORITY

This application claims priority under 35 USC 371 to International Application No. PCT/US2007/019588, filed on Sep. 7, 2007, which claims priority to U.S. Provisional Application Ser. No. 60/842,801, filed Sep. 7, 2006.

CROSS-REFERENCE

This application claims priority to U.S. Application No. 60/842,801, filed on Sep. 7, 2006.

TECHNICAL FIELD OF THE INVENTION

The present invention is directed to compounds which modulate interleukin-1 (IL-1) receptor-associated kinase (IRAK) and are useful in the prevention or treatment of inflammatory, cell proliferative and immune-related and conditions and diseases. The invention is also directed to pharmaceutical compositions comprising these compounds and the use of these compounds and compositions in the prevention or treatment of conditions or diseases mediated by IRAK.

BACKGROUND OF THE INVENTION

The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, *Cytokine Growth Factor Rev.*, 1997, 8: 253-265.

IL-1 treatment of cells induces the formation of a complex consisting of the two IL-1 receptor chains, IL-1R1 and IL-1RAcP, and the resulting heterodimer recruits an adaptor molecule designated as MyD88. See, e.g., Wesche et al., *J. Biol. Chem.*, 1999, 274: 19403-19410. MyD88 binds to a protein designated IRAK (IL-1 receptor associated kinase). See, e.g., O'Neill et al., *J. Leukoc. Biol.*, 1998, 63(6):650-657; Auron, *Cytokine Growth Factor Rev.*, 1998, 9(3-4): 221-237; and O'Neill, *Biochem. Soc. Trans.*, 2000, 28(5): 557-563. IRAK is subsequently phosphorylated and released from the receptor complex to interact with a tumor necrosis factor receptor-associated factor, TRAF6, which transduces the signal to downstream effector molecules. See, e.g., Cao et al., *Nature*, 1996, 383: 443-446. TRAF6 can trigger the NIK/IKK kinase cascade to activate the transcription factor NF-kappa B. NF-kappa B regulates a number of genes that, in turn, regulate immune and inflammatory responses.

Four IRAKs have been identified: IRAK-1 (see, e.g., Cao et al., *Science*, 1996, 271: 1128-1131), IRAK-2 (see, e.g., Muzio et al., *Science*, 1997, 278: 1612-1615), the monomyeloic cell-specific IRAK-M, also known as IRAK-3 (see, e.g., Wesche et al., *J. Biol. Chem.*, 1999, 274: 19403-10), and IRAK-4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., *J. Exp. Med.*, 1999, 189(7): 1129-1138) and LPS receptors (see, e.g., Yang et al., *J. Immunol.*, 1999, 163: 639-643; and Wesche et al., *J. Biol. Chem.*, 1999, 274: 19403-19410). Over-expression of IRAK-2 and IRAK-M has been shown to be capable of reconstituting the response to IL-1 and LPS in an IRAK deficient cell line.

The identification of compounds that modulate the function of IRAK proteins represents an attractive approach to the development of therapeutic agents for the treatment of inflammatory, cell proliferative and immune-related conditions and diseases associated with IRAK-mediated signal transduction, such as rheumatoid arthritis, inflammatory bowel disease, multiple sclerosis, diabetes, obesity, allergic disease, psoriasis, asthma, graft rejection, cancer, and sepsis.

SUMMARY OF THE INVENTION

The present invention provides compounds of Formula (I):

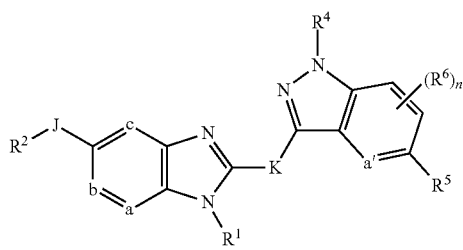

or a pharmaceutically acceptable salt thereof.

Referring to Formula (1), $R^1$ is an optionally substituted aliphatic, an optionally substituted cycloaliphatic, an optionally substituted heterocycloaliphatic, an optionally substituted aryl, or an optionally substituted heteroaryl;

$R^2$ is H, an optionally substituted aliphatic, an optionally substituted cycloaliphatic, an optionally substituted heterocycloaliphatic, an optionally substituted aryl, or an optionally substituted heteroaryl;

Each of a, a', b, and c is independently N or $C(R^3)$;

Each of $R^3$, $R^5$, and $R^6$ is independently H, an optionally substituted aliphatic, an optionally substituted alkoxy, acyl, halo, hydroxy, amino, nitro, cyano, guanadino, amidino, carboxy, sulfo, mercapto, sulfanyl, sulfonyl, sulfonyl, sulfonamide, amido, sulfamide, urea, thiourea, carbamoyl, cycloaliphatic, cycloalkyloxy, heterocycloaliphatic, heterocycloalkyloxy, aryl, aralkyl, aryloxy, aroyl, heteroaryl, heteroaralkyl, heteroaryloxy, or heteroaroyl;

$R^4$ is H;

K is —O—, —S(O)$_i$—, —N($R^{X'}$)—, —C(O)—, or —C($R^{X'}$)($R^{Y'}$)—;

J is a bond, —O—, —S(O)$_i$—, —N(R$^{X'}$)—, alkylene, —C(O)—, —C(O)—O—, —CO—NR$^{X'}$—, —(CH$_2$)$_p$—N(R$^{X'}$)—, or —N(R$^{X'}$)—C(O)—;

Each of R$^{X'}$ and R$^{Y'}$ is independently H or an optionally substituted aliphatic;

n is 0, 1, 2, or 3;

i is 0, 1, or 2; and p is 1, 2, 3, or 4;

provided that when R$^1$ is an unsubstituted alkyl and J is —O—, then R$^2$ is H, an optionally substituted aliphatic, an optionally substituted aryl, or an unsubstituted heteroaryl.

In some embodiments, K is —N(R$^{X'}$)—.

In some embodiments, R$^{X'}$ is H.

In some further embodiments, R$^1$ is an optionally substituted aliphatic, an optionally substituted cycloaliphatic, an optionally substituted bicycloaliphatic, or an optionally substituted heterocycloaliphatic. When R$^1$ is an optionally substituted aliphatic or optionally substituted cycloaliphatic, each of the substituents on R$^1$ independently can be halo, amino, sulfanyl, mercapto, oxo, hydroxyl, or alkoxy.

In some other embodiments, R$^1$ is an optionally substituted aryl or an optionally substituted heteroaryl. When R$^1$ is an optionally substituted aryl or an optionally substituted heteroaryl, each of the substituents on R$^1$ independently can be halo, amino, sulfanyl, mercapto, haloalkyl, cyano, nitro, haloalkoxy, hydroxyl, or alkoxy.

In still some further embodiments, R$^1$ is cyclohexyl, phenyl, or alkyl, each of which is optionally substituted with halo, hydroxy, amino, alkoxy, amido, alkoxy, or alkyl.

In some embodiments, J is a bond, —O—, —N(R$^{X'}$)—, alkylene (e.g., of 1 to 4 carbon atoms), —C(O)—, —C(O)—O—, —C(O)—N(R$^{X'}$)—, —(CH$_2$)$_p$—N(R$^{X'}$)—, or —N(R$^{X'}$)—C(O)—.

In some other embodiments, J is —O—.

In some other embodiments, J is a bond or an alkylene (e.g., of 1 to 4 carbon atoms).

In some other embodiments, J is —CH$_2$—.

In some embodiments, R$^2$ is H, an optionally substituted alkyl, an optionally substituted cycloalkyl, an optionally substituted heterocycloalkyl, an optionally substituted (cycloalkyl)alkyl, or an optionally substituted (heterocycloalkyl)alkyl.

In some embodiments, R$^2$-J- is H, an optionally substituted alkyl, an optionally substituted cycloalkyl, an optionally substituted heterocycloalkyl, an optionally substituted (cycloalkyl)alkyl, or an optionally substituted (heterocycloalkyl)alkyl.

In some other embodiments, R$^2$-J- is H, hydroxymethyl, 4-(2-(pyridin-4-yl)ethyl)piperazin-1-yl)-methyl), carbethoxy, morpholinomethyl, cyclopentylamido, isopentylamido, piperidinylmethyl, or pyrolidinecarbonyl.

In further embodiments, R$^5$ is an optionally substituted aryl or an optionally substituted heteroaryl. When R$^5$ is an optionally substituted aryl (e.g., phenyl) or an optionally substituted heteroaryl (e.g., pyridinyl), each of the substituents on R$^5$ independently can be halo, amino, sulfanyl, mercapto, sulfamido, haloalkyl, cyano, nitro, haloalkoxy, hydroxyl, or alkoxy.

In some embodiments, R$^5$ is (4-methoxy)pyridin-3-yl, 3-methoxymethylphenyl, 2-methoxyphenyl, 2-trifluromethoxyphenyl, or 3-aminophenyl, In some other embodiments, R$^5$ is H or halo (e.g., bromo).

In some embodiments, n is 0.

In other embodiments, n is 1.

In some embodiments, each of a, a', b, and c is independently C(R$^3$).

In some embodiments, R$^3$ is H.

In some embodiments, only one of a, a', b, and c is N.

In some embodiments, two and only two of a, a', b, and c are N.

In some further embodiments, R$^1$ is a cycloaliphatic optionally substituted with hydroxy; J is —CH$_2$— or —CH$_2$—N(R$^{X'}$)—; R$^5$ is optionally substituted phenyl or pyridyl; each of a, a', b and c is independently CH; and n is 0.

In some embodiments, J is —CH$_2$— and R$^2$ is an optionally substituted heterocycle containing at least one N (nitrogen atom) attached to J.

In some embodiments, R$^1$ is a cycloaliphatic optionally substituted with hydroxy; J is —C(O)R$^2$— or —CH$_2$—N(R$^{X'}$)—; R$^5$ is optionally substituted phenyl or pyridyl; each of a, a', b and c is independently CH; and n is 0.

In some embodiments, R$^2$ is an optionally substituted heterocycle containing at least one N (nitrogen atom) attached to J.

In some embodiments, R$^1$ is an aliphatic optionally substituted with hydroxy; R$^2$-J- is H; R$^5$ is H or halo; each of a, a', b, and c is independently CH; and n is 0.

In some embodiments, K is —NH—; R$^1$ is an alkyl (e.g., of 1 to 4 carbon atoms) or cyclohexyl, and is optionally substituted with hydroxy; J is a bond or —CH$_2$—; R$^2$ is an alkyl, cycloalkyl, or heterocycloalkyl; R$^5$ is heteroaryl or amino phenyl; and n is 0.

Examples of the compounds of Formula (1) include (2-(5-(3-aminophenyl)-1H-indazol-3-ylamino)-1-cyclohexyl-1H-benzo[d]imidazol-6-yl)methanol;

(1-cyclohexyl-2-(5-(3-(methoxymethyl)phenyl)-1H-indazol-3-ylamino)-1H-benzo[d]imidazol-5-yl)methanol;

4-(2-(5-(4-methoxypyridin-3-yl)-1H-indazol-3-ylamino)-5-((4-(2-(pyridin-4-yl)ethyl)piperazin-1-yl)methyl)-1H-benzo[d]imidazol-1-yl)cyclohexanol;

ethyl 1-((2-(5-(4-methoxypyridin-3-yl)-1H-indazol-3-ylamino)-1-(4-hydroxycyclohexyl)-1H-benzo[d]imidazol-5-yl)methyl)piperidine-4-carboxylate;

(2-(5-(4-methoxypyridin-3-yl)-1H-indazol-3-ylamino)-1-phenyl-1H-benzo[d]imidazol-5-yl)methanol;

N-(1-cyclohexyl-5-(morpholinomethyl)-1H-benzo[d]imidazol-2-yl)-5-(4-methoxypyridin-3-yl)-1H-indazol-3-amine;

2-(5-(2-methoxyphenyl)-1H-indazol-3-ylamino)-N-cyclopentyl-1-(4-hydroxycyclohexyl)-1H-benzo[d]imidazole-5-carboxamide;

1-(4-hydroxycyclohexyl)-N-isopentyl-2-(5-(2-methoxyphenyl)-1H-indazol-3-ylamino)-1H-benzo[d]imidazole-5-carboxamide;

(1-(4-hydroxycyclohexyl)-2-(5-(2-methoxyphenyl)-1H-indazol-3-ylamino)-1H-benzo[d]imidazol-5-yl)(pyrrolidin-1-yl)methanone;

N-cyclopentyl-1-(4-hydroxycyclohexyl)-2-(5-(2-(trifluoromethoxy)phenyl)-1H-indazol-3-ylamino)-1H-benzo[d]imidazole-5-carboxamide;

2-(5-(2-(trifluoromethoxy)phenyl)-1H-indazol-3-ylamino)-1-(4-hydroxycyclohexyl)-N-isopentyl-1H-benzo[d]imidazole-5-carboxamide;

ethyl 1-(4-hydroxycyclohexyl)-2-(5-(4-methoxypyridin-3-yl)-1H-indazol-3-ylamino)-1H-benzo[d]imidazole-5-carboxylate;

4-(5-(hydroxymethyl)-2-(5-(4-methoxypyridin-3-yl)-1H-indazol-3-ylamino)-1H-benzo[d]imidazol-1-yl)cyclohexanol;

(1-cyclohexyl-2-(5-(4-methoxypyridin-3-yl)-1H-indazol-3-ylamino)-1H-benzo[d]imidazol-5-yl)methanol;

N-(1-cyclohexyl-5-(piperidin-1-ylmethyl)-1H-benzo[d]imidazol-2-yl)-5-(4-methoxypyridin-3-yl)-1H-indazol-3-amine;

3-(2-(5-(4-methoxypyridin-3-yl)-1H-indazol-3-ylamino)-1H-benzo[d]imidazol-1-yl)propan-1-ol; and 3-(2-(5-bromo-1H-indazol-3-ylamino)-1H-benzo[d]imidazol-1-yl)propan-1-ol.

The invention further provides pharmaceutical compositions each containing a compound of Formula (I) described or specifically listed above and methods of using a compound of Formula (I) to modulate the function of IRAK proteins for the treatment of inflammatory, cell proliferative and immune-related conditions or diseases associated with IRAK-mediated signal transduction in a subject in need of such a treatment, such as rheumatoid arthritis, inflammatory bowel disease, multiple sclerosis, diabetes, obesity, allergic disease, psoriasis, asthma, graft rejection, cancer, and sepsis.

The invention still further provides a method of treating rheumatoid arthritis, multiple sclerosis, sepsis, osteoarthritis, inflammatory bowel disease, osteoporosis, myasthenia gravis, stroke, Alzheimer's disease, Parkinson's disease, cardiac contractile dysfunction, type I diabetes, type II diabetes, familial cold autoinflammatory syndrome, allergic disease, cancer, psoriasis, asthma, or graft rejection in a subject in need of such a treatment, which in the method includes administering to the subject a therapeutically effective amount of a compound of Formula (I).

The invention further provides a method of treating an IRAK-responsive condition or disorder, a condition or disorder mediated by IRAK, or a condition or disorder mediated by NF-kappa B in a subject in need of such a treatment, wherein the method includes administering to the subject a therapeutically effective amount of a compound of Formula (I). Examples of such a condition or disorder include rheumatoid arthritis, inflammatory bowel disease, allergic disease, cancer, psoriasis, asthma, multiple sclerosis, graft rejection, and sepsis.

In some embodiments, the compound of Formula (I) is administered orally, parenterally, or topically.

In some other embodiments, the compound is administered in combination with a second therapeutic agent. Examples of such a seond therapeutic agent include methotrexate, sulfasalazine, a COX-2 inhibitor, hydroxychloroquine, cyclosporine A, D-penicillamine, infliximab, etanercept, auranofin, aurothioglucose, sulfasalazine, sulfasalazine analogs, mesalamine, corticosteroids, corticosteroid analogs, 6-mercaptopurine, cyclosporine A, methotrextate and infliximab, interferon beta-1 beta, interferon beta-1 alpha, azathioprine, glatiramer acetate, a glucocorticoid, and cyclophosphamide.

The invention further provides a method for modulating IRAK, which includes contacting a cell or an IRAK protein with any of the compounds described above. In some endomuments, the compounds inhibit IRAK. In some other embodiments, the compounds activate IRAK The invention further provides a method for decreasing NF-kappa B activation in a cell, which includes contacting the cell with any of the compounds described above.

For purposes of this invention, the chemical elements are identified in accordance with the Periodic Table of the Elements, CAS version, *Handbook of Chemistry and Physics*, 75$^{th}$ Ed. Additionally, general principles of organic chemistry are described by Thomas Sorrell in *Organic Chemistry*, University Science Books, Sausalito (1999); and by M. B. Smith and J. March in *Advanced Organic Chemistry*, 5$^{th}$ Ed., John Wiley & Sons, New York (2001), the entire contents of which are hereby incorporated by reference.

The term "modulating" as used herein means either increasing or decreasing, e.g. activity, by a measurable amount. Compounds that modulate the function of IRAK proteins by increasing their activity are also called agonists, whereas compounds that modulate the function of IRAK proteins by decreasing their activity are also called antagonists.

As used herein, the phrase "treating or reducing the severity of an IRAK mediated disease" refers both to treatments for diseases that are directly caused by IRAK activities and alleviation of symptoms of diseases not directly caused by IRAK activities.

As used herein, the term "aliphatic" encompasses the terms alkyl, alkenyl, and alkynyl, each of which is optionally substituted as set forth below.

As used herein, an "alkyl" group refers to a saturated aliphatic hydrocarbon group containing 1 to 8 (e.g., 1 to 6 or 1 to 4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, and 2-ethylhexyl. An alkyl group can be substituted (i.e., is optionally substituted) with one or more substituents such as halo; cycloaliphatic (e.g., cycloalkyl or cycloalkenyl); heterocycloaliphatic (e.g., heterocycloalkyl or heterocycloalkenyl); aryl; heteroaryl; alkoxy; aroyl; heteroaroyl; acyl (e.g., (aliphatic)carbonyl, (cycloaliphatic)carbonyl, or (heterocycloaliphatic)carbonyl); nitro; cyano; amido (e.g., (cycloalkylalkyl)amido, arylamidoo, aralkylamido, (heterocycloalkyl)amido, (heterocycloalkylalkyl)amido, heteroarylamido, heteroaralkylamido alkylamido, cycloalkylamido, heterocycloalkylamido, arylamido, or heteroarylamido); amino (e.g., aliphaticamino, cycloaliphaticamino, or heterocycloaliphaticamino); sulfonyl (e.g., aliphatic-S(O)$_2$—); sulfinyl; sulfanyl; sulfoxy; urea; thiourea; sulfonamide; sulfamide; oxo; carboxy; carbamoyl; cycloaliphaticoxy; heterocycloaliphaticoxy; aryloxy; heteroaryloxy; aralkyloxy; heteroarylalkoxy; alkoxycarbonyl; alkylcarbonyloxy; or hydroxy. Without limitation, examples of substituted alkyls include carboxyalkyl (such as HO—(O)—C-alkyl, alkoxycarbonylalkyl, and alkylcarbonyloxyalkyl); cyanoalkyl; hydroxyalkyl; alkoxyalkyl; acylalkyl; aralkyl; (alkoxyaryl)alkyl; (sulfortylamino)alkyl (e.g., alkyl-S(O)$_2$-aminoalkyl); aminoalkyl; amidoalkyl; (cycloaliphatic)alkyl; silyl (e.g. trialkylsilyl); and haloalkyl.

As used herein, an "alkenyl" group refers to an aliphatic carbon group that contains 2 to 8 (e.g., 2 to 6 or 2 to 4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents, such as halo; cycloaliphatic (e.g., cycloalkyl or cycloalkenyl); heterocycloaliphatic (e.g., heterocycloalkyl or heterocycloalkenyl); aryl; heteroaryl; alkoxy; aroyl; heteroaroyl; acyl (e.g., (aliphatic)carbonyl, (cycloaliphatic)carbonyl, or (heterocycloaliphatic)carbonyl); nitro; cyano; amido (e.g., (cycloalkylalkyl)amido, arylamido, aralkylamido, (heterocycloalkyl) amido, (heterocycloalkylalkyl)amido, heteroarylamido, heteroaralkylamido alkylaminocarbonyl, cycloalkylaminocarbonyl, heterocycloalkylaminocarbonyl, arylaminocarbonyl, or heteroarylaminocarbonyl); amino (e.g., aliphaticamino, cycloaliphaticamino, heterocycloaliphaticamino, or aliphaticsulfonylamino); sulfonyl (e.g., alkyl-S(O)$_2$—, cycloaliphatic-S(O)$_2$—, or aryl-S(O)$_2$—); sulfinyl; sulfanyl; sulfoxy; urea; thiourea; sulfonamide; sulfamide; oxo; carboxy; carbamoyl; cycloaliphaticoxy; heterocycloaliphaticoxy; aryloxy; heteroaryloxy; aralkyloxy; heteroaralkoxy; alkoxycarbonyl; alkylcarbonyloxy; or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-S(O)$_2$-aminoalkenyl), aminoalkenyl, amidoalkenyl, (cycloaliphatic)alkenyl, and haloalkenyl.

As used herein, an "alkynyl" group refers to an aliphatic carbon group that contains 2 to 8 (e.g., 2 to 6 or 2 to 4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl; heteroaroyl; alkoxy; cycloalkyloxy; heterocycloalkyloxy; aryloxy; heteroaryloxy; aralkyloxy; nitro; carboxy; cyano; halo; hydroxy; sulfo; mercapto; sulfanyl (e.g., aliphatic-S— or cycloaliphatic-S—); sulfinyl (e.g., aliphatic-S(O)— or cycloaliphatic-S(O)—); sulfonyl (e.g., aliphatic-S(O)$_2$—, aliphaticamino-S(O)$_2$—, or cycloaliphatic-S(O)$_2$—); amido (e.g., alkylamido, alkylamido, cycloalkylamido, heterocycloalkylamido, cycloalkylamido, arylamido, arylamido, aralkylamido, (heterocycloalkyl)amido, (cycloalkylalkyl)amido, heteroaralkylamido, heteroarylamido or heteroarylamido); urea; thiourea; sulfonamide; sulfamide; alkoxycarbonyl; alkylcarbonyloxy; cycloaliphatic; heterocycloaliphatic; aryl; heteroaryl; acyl (e.g., (cycloaliphatic)carbonyl or (heterocycloaliphatic)carbonyl); amino (e.g., aliphaticamino); sulfoxy; oxo; carbamoyl; (cycloaliphatic)oxy; (heterocycloaliphatic)oxy; or (heteroaryl)alkoxy.

As used herein, the term "amido" encompasses both "aminocarbonyl" and "carbonylamino." Each of these terms, when used alone or in connection with another group, refers to an amido group such as —N(R$^X$)—C(O)—R$^Y$ or —C(O)—N(R$^X$)$_2$, when used terminally; or —C(O)—N(R$^X$)— or —N(R$^X$)—C(O)— when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, and cycloalkylamido.

As used herein, an "amino" group refers to —N(R$^X$)(R$^Y$) wherein each of R$^X$ and R$^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfonyl, (aliphatic)carbonyl, (cycloaliphatic)carbonyl, ((cycloaliphatic)aliphatic)carbonyl, aryl carbonyl, (araliphatic)carbonyl, (heterocycloaliphatic) carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, arylamino, and diarylamino. When the term "amino" is not the terminal group (e.g., alkylcarbonylamino), it is represented by —N(R$^X$)—. R$^X$ has the same meaning as defined above.

As used herein, an "aryl" group, used alone or as part of a larger moiety such as in "aralkyl", "aralkoxy," or "aryloxyalkyl," refers to monocyclic (e.g., phenyl); bicyclic (e.g., indenyl, naphthalenyl, tetrahydronaphthyl, or tetrahydroindenyl); and tricyclic (e.g., fluorenyl tetrahydrofluorenyl, tetrahydroanthracenyl, or anthracenyl) ring systems in which the monocyclic ring system is aromatic or at least one of the rings in a bicyclic or tricyclic ring system is aromatic. The bicyclic and tricyclic groups include benzofused 2- or 3-membered carbocyclic rings. For instance, a benzofused group includes phenyl fused with two or more C$_{4-8}$ carbocyclic moieties. An aryl is optionally substituted with one or more substituents including aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl (e.g., aliphaticcarbonyl, (cycloaliphatic)carbonyl, ((cycloaliphatic)aliphatic) carbonyl, (araliphatic)carbonyl, (heterocycloaliphatic)carbonyl, ((heterocycloaliphatic)aliphatic)carbonyl, or (heteroaraliphatic)carbonyl); sulfonyl (e.g., aliphatic-S(O)$_2$— or amino-S(O)$_2$—); sulfinyl (e.g., aliphatic-S(O)— or cycloaliphatic-S(O)—); sulfanyl (e.g., aliphatic-S—); cyano; halo; hydroxy; mercapto; sulfoxy; urea; thiourea; sulfonamide; sulfamide; or carbamoyl. Alternatively, an aryl can be unsubstituted.

Non-limiting examples of substituted aryls include haloaryl (e.g., mono-, di (e.g., p,m-dihaloaryl), and (trihalo) aryl); (carboxy)aryl (e.g., (alkoxycarbonyl)aryl, ((aralkyl) carbonyloxy)aryl, and (alkoxycarbonyl)aryl); (amido)aryl (e.g., (aminocarbonyl)aryl, (((alkylamino)alkyl)aminocarbonyparyl, (alkylcarbonyl)aminoaryl, (arylaminocarbonyl) aryl, and (((heteroarypamino)carbonyl)aryl); aminoaryl (e.g., ((alkylsulfonyl)amino)aryl or ((dialkyl)amino)aryl); (cyanoalkyl)aryl; (alkoxy)aryl; (sulfonamide)aryl (e.g., (aminosulfonyl)aryl); (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl) aryl; (((alkylsulfonyl)amino)alkyl)aryl; ((heterocycloaliphatic)carbonyl)aryl; ((alkylsulfonyl)alkyl) aryl; (cyanoalkyl)aryl; (hydroxyalkyl)aryl; (alkylcarbonyl) aryl; alkylaryl; (trihaloalkyl)aryl; p-amino-m-alkoxycarbonylaryl; p-amino-m-cyanoaryl; p-halo-m-aminoaryl; and (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic," "alkyl," and "aryl" are as defined herein. An example of an araliphatic such as an aralkyl group is benzyl.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic (e.g., alkyl, alkenyl, or alkynyl, including carboxyalkyl, hydroxyalkyl, or haloalkyl such as trifluoromethyl); cycloaliphatic (e.g., cycloalkyl or cycloalkenyl); (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido (e.g., alkylamido, cycloalkylamido, (cycloalkylalkyl)amido, arylamido, aralkylamido, (heterocycloalkyl)amido, (heterocycloalkylalkyl)amido, heteroarylamido, or heteroaralkylamido); cyano; halo; hydroxy; acyl; mercapto; alkylsulfanyl; sulfoxy; urea; thiourea; sulfonamide; sulfamide; oxo; or carbamoyl.

As used herein, a "bicyclic ring system" includes 8 to 12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bi-cyclic (fused or bridged) ring of 3 to 10 (e.g., 5 to 10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1 ]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic (e.g., alkyl, alkenyl, or alkynyl); cycloaliphatic; (cycloaliphatic)aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl); cyano; halo; hydroxy; mercapto; sulfonyl (e.g., alkyl-S(O)$_2$— and aryl-S(O)$_2$—); sulfinyl (e.g., alkyl-S(O)—); sulfanyl (e.g., alkyl-S—); sulfoxy; urea; thiourea; sulfonamide; sulfamide; oxo; or carbamoyl.

As used herein, the term "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3.7}$]nonyl. A monocyclic heterocycloalkyl group can be fused with a phenyl moiety such as tetrahydroisoquinoline.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl); nitro; cyano; halo; hydroxy; mercapto; sulfonyl (e.g., alkylsulfonyl or arylsulfonyl); sulfonyl (e.g., alkylsulfinyl); sulfanyl (e.g., alkylsulfanyl); sulfoxy; urea; thiourea; sulfonamide; sulfamide; oxo; or carbamoyl.

A "heteroaryl" group, as used herein, refers to a monocyclic, bicyclic, or tricyclic ring system having 4 to 15 ring atoms wherein at least one of the ring atoms is a heteroatom (e.g., N, O, S, or combinations thereof and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4- to 8-membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, and 1,8-naphthyridyl.

Without limitation, examples of monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, and 1,3,5-triazyl. Monocyclic heteroaryls are numbered according to standard chemical nomenclature.

Without limitation, examples of bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, and pteridyl. Bicyclic heteroaryls are numbered according to standard chemical nomenclature.

A heteroaryl is optionally substituted with one or more substituents such as aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl (e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl); sulfonyl (e.g., aliphatic- S(O)$_2$— or amino-S(O)$_2$—); sulfonyl (e.g., aliphatic-S(O)—); sulfanyl (e.g., aliphatic-S—); nitro; cyano; halo; hydroxy; mercapto; sulfoxy; urea; thiourea; sulfonamide; sulfamide; or carbamoyl. Alternatively, a heteroaryl can be unsubstituted.

Non-limiting examples of substituted heteroaryls include (halo)heteroaryl (e.g., mono- and di-(halo)heteroaryl); (carboxy)heteroaryl (e.g., (alkoxycarbonyl)heteroaryl); cyanoheteroaryl; aminoheteroaryl (e.g., ((alkylsulfonyl)amino)heteroaryl and((dialkyl)amino)heteroaryl); (amido)heteroaryl (e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl); (cyanoalkyl)heteroaryl; (alkoxy)heteroaryl; (sulfonamide)heteroaryl (e.g., (aminosulfonyl)heteroaryl); (sulfonyl)heteroaryl (e.g., (alkylsulfonyl)heteroaryl); (hydroxyalkyl)heteroaryl; (alkoxyalkyl)heteroaryl; (hydroxy)heteroaryl; ((carboxy)alkyl)heteroaryl; (((dialkyl)arnino)alkyl)heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl (e.g., (alkylcarbonyl)heteroaryl); (alkyl)heteroaryl, and (haloalkyl)heteroaryl (e.g., trihaloalkylheteroaryl).

A "heteroaraliphatic" group (e.g., a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (e.g., carboxyalkyl, hydroxyalkyl, and haloalkyl such as trifluoromethyl); alkenyl; alkynyl; cycloalkyl; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; aminocarbonyl; alkylcarbonylamino; cycloalkylcarbonylamino; (cycloalkylalkyl)carbonylamino; arylcarbonylamino; aralkylcarbonylamino; (heterocycloalkyl)carbonylamino; (heterocycloalkylalkyl)carbonylamino; heteroarylcarbonylamino; heteroaralkylcarbonylamino; cyano; halo; hydroxy; acyl; mercapto; alkylsulfanyl; sulfoxy; urea; thiourea; sulfonamide; sulfamide; oxo; or carbamoyl.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" group refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group wherein "alkyl" has been defined previously.

As used herein, a "carbamoyl" group refers to a group having the structure —O—CO—NR$^X$R$^Y$ or —NR$^X$—CO—O—R$^Z$, wherein $R^X$ and $R^Y$ are as defined above and $R^Z$ can be aliphatic, aryl, aralphatic, heterocycloaliphatic, heteroaryl, or heteroaraliphatic.

As used herein, a "carboxy" group refers to —COOH, —COOR$^X$, —O—C(O)H, —OC(O)R$^X$ when used as a terminal group; or —O—C(O)— or —C(O)—O— when used as an internal group.

As used herein, a "haloaliphatic" group refers to an aliphatic group substituted with 1 to 3 halogen atoms. For instance, the term haloalkyl includes the group —CF$_3$.

As used herein, a "mercapto" group refers to —SH.

As used herein, a "sulfo" group refers to —S(O)$_3$—H or —S(O)$_3$—R$^X$ when used terminally or —S(O)$_3$— when used internally.

As used herein, a "sulfamide" group refers to the structure —N(R$^X$)—S(O)$_2$—N(R$^Y$)(R$^Z$) when used terminally and —N(R$^X$)—S(O)$_2$—N(R$^Y$)— when used internally, wherein $R^X$, $R^Y$, and $R^Z$ have been defined above.

As used herein, a "sulfonamide" group refers to the structure —S(O)$_2$—N(R$^X$)(R$^Y$) or —N(R$^X$)—S(O)$_2$—R$^Z$ when used terminally; or —S(O)$_2$—N(R$^X$)— or —N(R$^X$)—S(O)$_2$— when used internally, wherein $R^X$, $R^Y$, and $R^Z$ are defined above.

As used herein a "sulfanyl" group refers to —S—R$^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein $R^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to-S(O)$_2$—R$^X$ when used terminally and —S(O)$_2$— when used internally, wherein $R^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$-or the like.

As used herein, a "sulfoxy" group refers to —O—S(O)—R$^X$ or —S(O)—O—R$^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —N(R$^X$)—CO—N(R$^Y$)(R$^Z$) and a "thiourea" group refers to the structure —N(R$^X$)—CS—N(R$^Y$)(R$^Z$) when used terminally and —N(R$^X$)—CO—N(R$^Y$)— or —N(R$^X$)—C(S)—N(R$^Y$)— when used internally, wherein $R^X$, $R^Y$, and $R^Z$ have been defined above.

As used herein, a "guanidine" group refers to —N=C(N(R$^X$)(R$^Y$))(N(R$^X$)(R$^Y$)) or —N(R$^X$)=C(N(R$^X$)(R$^Y$))(N(R$^X$)(R$^Y$)), wherein $R^X$ and $R^Y$ have been defined above.

As used herein, the term "amidino" refers to the structure —C(=N(R$^X$))(N(R$^X$)(R$^Y$)) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^xO(O)C$-alkyl, is an example of a carboxy group used terminally. A group is internal when the group is present in the middle of a substituent to at the end of the substituent bound to the rest of the chemical structure. Alkylcarboxy (e.g., alkyl-C(O)—O— or alkyl-O—C(O)—) and alkylcarboxyaryl (e.g., alkyl-C(O)—O-aryl- or alkyl-O—(CO)-aryl-) are examples of carboxy groups used internally.

As used herein, the term "cyclic group" encompasses mono-, bi-, and tri-cyclic ring systems including cycloaliphatic, heterocycloaliphatic, aryl, or heteroaryl, each of which has been previously defined.

As used herein, the term "bridged bicyclic ring system" refers to a bicyclic heterocyclicalipahtic ring system or bicyclic cycloaliphatic ring system in which the rings have at least two common atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxatricyclo[3.3.1.0$^{3.7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfonamide, sulfamide, oxo, or carbamoyl.

As used herein, the term "aliphatic chain" refers to a branched or straight aliphatic group (e.g., alkyl groups, alkenyl groups, or alkynyl groups). A straight aliphatic chain has the structure —(CH$_2$)$_v$—, wherein v is 1 to 6. A branched aliphatic chain is a straight aliphatic chain that is substituted with one or more aliphatic groups. A branched aliphatic chain has the structure —[CHQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents as chemically allowed, such as are illustrated generally above, or as exemplified by particular classes, subclasses, and species of the invention. As described herein, the variables $R_1$, $R_2$, and $R_3$, and other variables contained therein formula (I) encompass specific groups, such as alkyl and aryl. Unless otherwise noted, each of the specific groups for the variables $R_1$, $R_2$, and $R_3$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, New York, 537 (1970). As used herein, a "patient" refers to a mammal, including a human.

As used herein, a "subject" for treatment genrally refers and thus may be interchangeable with a "patient," such as an animal (e.g., a mammal such as a human).

Unless otherwise stated, the structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

DETAILED DESCRIPTION OF THE INVENTION

In general, the invention features compounds of Formula (I), which modulate the function of IRAK proteins.

Synthesis of Compounds of Formula (I)

Compounds of Formula (I) may be synthesized from commercially available or known starting materials by known methods. Exemplary synthetic routes to produce compounds of Formulae (I) are provided in Schemes 1-4 below. The generic schemes are not limiting and can be applied to preparation of other compounds having different variables.

Scheme 1 below depicts a general route for the synthesis of compounds of formula (I) wherein K is NR$^{X'}$, O, or S.

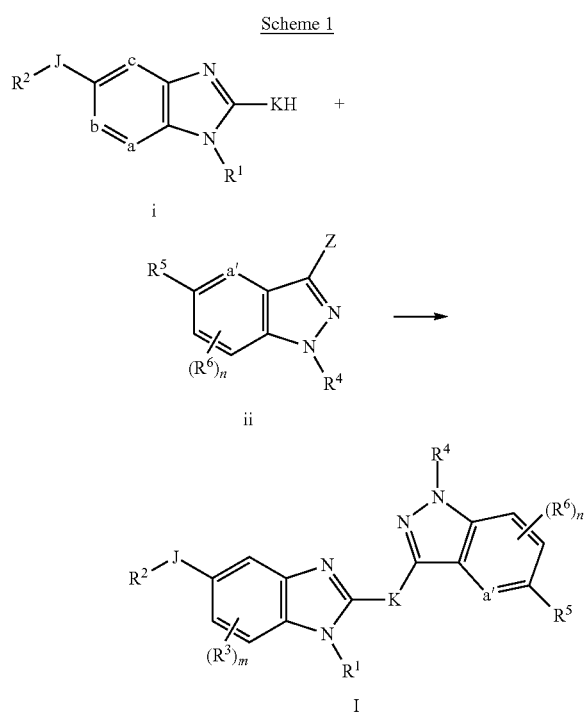

Refering to Scheme 1, Z is a leaving group such as, for example, halogen, e.g. iodine, or a sulfonate ester, the benzimidazole i reacts with an indazole ii in the presence of a palladium catalyst such as, for example, Pd$_2$(dba)$_2$ in the presence of a ligand such as, for example, xantphos to provide compounds of formula (I). Alternatively, the coupling of i with ii may be achieved using a copper catalyst such as, for example, copper iodide in the presence of a diamine ligand such as, for example, N$^1$,N$^2$-dimethylcyclohexane-1,2-diamine. See, e.g., J. C. Antilla, J. M. Baskin, T. E. Barder, S. L. Buchwald, *J. Org. Chem.*, 2004, 69, 5578-5587.

The benzimidazoles of Formula (I) as used in Scheme 1, wherein K is NR$^{X'}$, O, or S can be prepared by known methods such as, for example, as illustrated in Scheme 2.

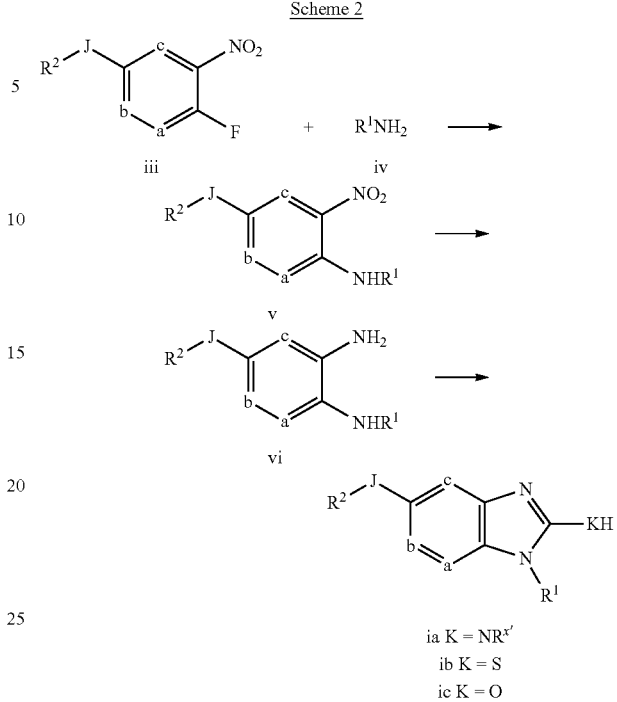

In Scheme 2, a nitro-fluoro compound of formula iii is reacted with an amine of formula iv, optionally in the presence of microwave irradiation, to provide a compound of formula v. Reduction of the nitro group in formula v by, for example, known hydrogenation conditions such as hydrogen in the presence of palladium on carbon, provides the diamine of formula vi. Reaction of the diamine vi with cyanogen bromide provides the benzimidazole of formula ia. Reaction of the diamine vi with carbon disulfide provides the benzimidazole of formula ib (Valdez, J., et al., *Bioorganic and Medicinal Chemistry Letters*, 2002, 2221). Reaction of the diamine vi with carbonyl diimidazole provides the benzamidazole of formula ic (Mewshaw, R. E. et al., *Bioorganic and Medicinal Chemistry Letters*, 2002, 271).

In some embodiments, wherein K is —CH$_2$— or —C(O)—, the benzimidazoles of formula id and ie are prepared as illustrated in Scheme 3.

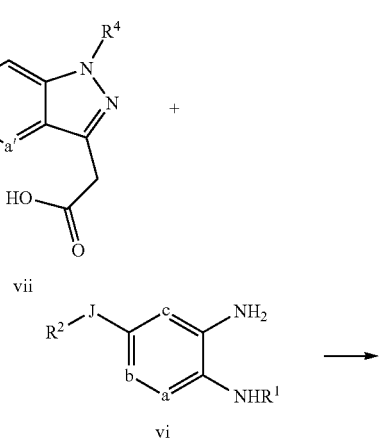

-continued

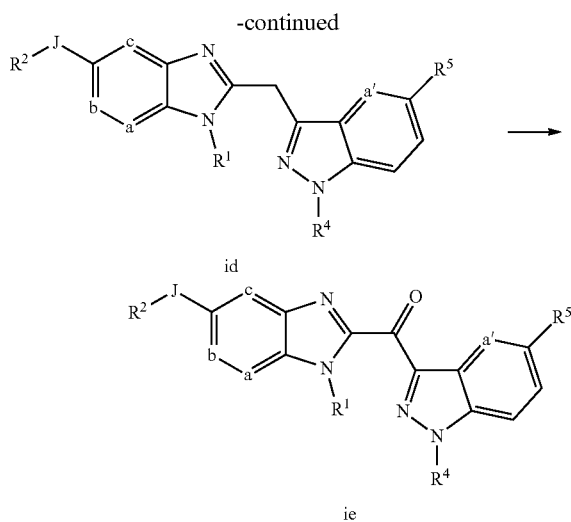

Refering to Scheme 3, the indazole acetic acid vii reacts with the benzimidazole vi in the presence of an acid catalyst at elevated temperatures to provide the benzimidazole-indazole id. See, e.g., C. Ainsworth, *J. Amer. Chem Soc.,* 1958, 80: 967-970. Oxidation of id using, for example, procedures previously described provides the benzimidazole-indazole-ketone ie. See, e.g., *J. Het. Chem.,* 1986, 1109-1113.

In some embodiments wherein $R^5$ is, e.g., a halogen, further modifications can be made to provide additional examples of Formula (I) as illustrated in Scheme 4.

Scheme 4

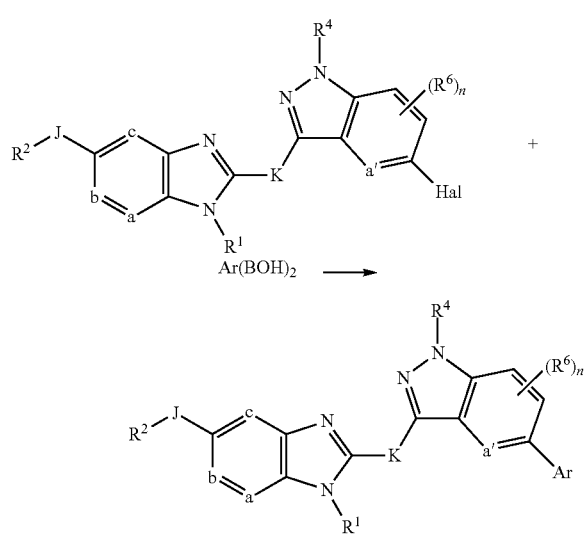

Referring to Scheme 4, reaction of a compound of Formula (I) wherein $R^5$ is, for example, bromo, with an aryl or heteroaryl boronic acid in the presence of a palladium catalyst, provides compounds of Formula (I) wherein $R^5$ is an optionally substituted aryl or heteroaryl compound.

In other embodiments, further examples of compounds of Formula (I) may be prepared by modification of $R^2$ wherein $R^2$ is, e.g., an amine, alcohol, aldehyde or carboxylate derivative.

Specific illustrations of compounds prepared by the methods described above are provided in the examples below.

Compositions, Administration, and Uses of Compounds of Formula (I)

A. Pharmaceutically Acceptable Compositions

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Examples of prodrugs include those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quatemization of any basic nitrogen-containing groups of the compounds disclosed herein. Water or oil-soluble or dispersible products may be obtained by such quatemization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, infrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

B. Administration of Compositions Containing Compounds of Formula (I)

As defined above, an effective amount is the amount required to confer a therapeutic effect on the treated patient. For a compound of Formula (I), an effective amount can range, for example, from about 1 mg/kg to about 150 mg/kg (e.g., from about 1 mg/kg to about 100 mg/kg). The effective amount may also vary, as recognized by those skilled in the art, dependant on route of administration, excipient usage, and the possibility of co-usage with other therapeutic treatments including use of other therapeutic agents and/or radiation therapy.

The amount of the compounds. of the present invention that may be combined with the carrier materials to produce a composition in a single dosage form will vary depending upon the host treated, the particular mode of administration. For instance, the compositions may be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

Compounds of Formula (I) can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The pharmaceutically acceptable compositions include aqueous solutions of the active agent, in an isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. As to route of administration, the compositions can be administered orally, intranasally, transdermally, intradermally, vaginally, intraaurally, intraocularly, buccally, rectally, transmucosally, or via inhalation, implantation (e.g., surgically), or intravenous administration. The compositions can be administered to an animal (e.g., a mammal such as a human, non-human primate, horse, dog, cow, pig, sheep, goat, cat, mouse, rat, guinea pig, rabbit, hamster, gerbil, or ferret, or a bird, or a reptile such as a lizard).

In certain embodiments, the compounds of Formula (I) can be administered by any method that permits the delivery of the compound to combat vascular injuries. For instance, the compounds of formula (I) can be delivered by any method described above. Additionally, the compounds of formula (I) can be administered by implantation (e.g., surgically) via an implantable device. Examples of implantable devices include, but are not limited to, stents, delivery pumps, vascular filters, and implantable control release compositions. Any implantable device can be used to deliver the compound provided that (i) the device, compound and any pharmaceutical composition including the compound are biocompatible, and (ii) that the device can deliver or release an effective amount of the compound to confer a therapeutic effect on the treated patient.

Delivery of therapeutic agents via stents, delivery pumps (e.g., mini-osmotic pumps), and other implantable devices is known in the art. See, e.g, Hofma, et al., *Current Interventional Cardiology Reports,* 3: 28-36 (2001), the entire contents of which, including references cited therein, are incorporated herein. Other descriptions of implantable devices, such as stents, can be found in U.S. Pat. Nos. 6,569,195 and 6,322,847; and PCT International Publication Numbers WO04/0044405, WO04/0018228, WO03/0229390, WO03/0228346, WO03/0225450, WO03/0216699, and WO03/0204168, each of which is also incorporated herein in by reference its entirety.

A delivery device, such as stent, includes a compound of formula (I). The compound may be incorporated into or onto the stent using methodologies known in the art. In some embodiments, a stent can include interlocked meshed cables. Each cable can include metal wires for structural support and polyermic wires for delivering the therapeutic agent. The polymeric wire can be dosed by immersing the polymer in a solution of the therapeutic agent. Alternatively, the therapeutic agent can be embedded in the polymeric wire during the formation of the wire from polymeric precursor solutions. In other embodiments, stents or implatable devices can be coated with polymeric coatings that include the therapeutic agent. The polymeric coating can be designed to control the release rate of the therapeutic agent.

Controlled release of therapeutic agents can utilize various technologies. Devices are known having a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The implantable device coating can include a blend of polymers each having a different release rate of the therapeutic agent. For instance, the coating can include a polylactic acid/polyethylene oxide (PLA-PEO) copolymer and a polylactic acid/polycaprolactone (PLA-PCL) copolymer. The polylactic acid/polyethylene oxide (PLA-PEO) copolymer can exhibit a higher release rate of therapeutic agent relative to the polylactic acid/polycaprolactone (PLA-PCL) copolymer. The relative amounts and dosage rates of therapeutic agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The stent can be coated by spraying the stent with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the stent body.

Optionally, compounds of Formula (I) can be administered in conjunction with one or more other agents that inhibit the TGFβ signaling pathway or treat the corresponding pathological disorders (e.g., fibrosis or progressive cancers) by way of a different mechanism of action. Examples of these agents include angiotensin converting enzyme inhibitors, nonsteroid and steroid anti-inflammatory agents, as well as agents that antagonize ligand binding or activation of the TGIFβ receptors, e.g., anti-TGFβ, anti-TGFβ receptor antibodies, or antagonists of the TGFβ type II receptors.

C. Use of Compounds of Formula (I)

According to yet another embodiment, the present invention provides a method of treating or reducing the severity of a disease in a patient by using a compound of formula (I) as described above, wherein said disease is selected from IRAK mediated pathologies, such as rheumatoid arthritis, multiple sclerosis, sepsis, osteoarthritis, inflammatory bowel disease, osteoporosis, myasthenia gravis, stroke, Alzheimer's disease, Parkinson's disease, cardiac contractile dysfunction, type I diabetes, type II diabetes or familial cold autoinflammatory syndrome, allergic disease, cancer, psoriasis, asthma, or graft rejection.

The efficacy of this method of treatment may be correlated to the activity of a compound of formula (I) in modulating the kinase activity of IRAK4 to phosphorylate IRAK1 peptide, which can be determined by methods known in the art. For instance, biotin labeled IRAK1, AA358-389, can be phosphorylated (in Ser and Thr positions) by IRAK4, followed by a detection step that uses TR-FRET as the tool for detecting phosphorylation. The FRET signal is generated by a mixture of two antibodies that bind to the phosphorylated Threonines in IRAK1 (e.g., Rabbit derived polyclonal anti-p-thr and Eu-anti rabbit IgG) and SA-APC that will bind to the biotin-peptide. Eu (the donor) is excited, e.g., at 340 ηm and the fluorescence energy is transferred to APC (the acceptor), e.g., at 615 ηm, which in turn is excited and emits, e.g., at 665 ηm.

All references cited within this document are incorporated herein in their entirety by reference.

EXAMPLES

In order that the invention described herein may be more fully understood, the following examples are set forth. It should be understood that these examples are for illustrative purposes only and are not to be construed as limiting this invention in any manner.

$^{1}$H-NMR spectra were generally recorded at 300 MHz using a Bruker AMX-300 instrument. Mass spectroscopy samples were analyzed on a MicroMass ZQ or Quattro II mass spectrometer operated in single MS mode with electrospray ionization. Samples were introduced into the mass spectrometer using chromatography, using Zorbax SB C18 column, 3.0×150 mm. Flow rate: 1.0 mL/minute. Detection: 254 & 214 nm. Mobile phase for all mass spectroscopy analysis consisted of acetonitrile-water mixtures with 0.2% formic acid as a modifier using 10-90% acetonitrile and water gradient. As used herein, the term "$R_t$" refers to the HPLC retention time, in minutes, associated with the compound. HPLC purification refers to C-18 reverse phase using a Gilson instrument, YMC combiprep ProC18 column, 20×100 mm. Flow rate was 20 mL/minute. Mobile phase consisted of water with 0.1% TFA and acetonitrile with 0.1% TFA. Running time was 10 minutes.

Compound names herein are consistent with the computer program ChemDraw Ultra, Version 9.0.1, program (see www.cambridgesoft.com).

Preparation 1

5-Bromo-3-iodo-2-(2-trimethylsilanyl-ethoxymethyl)-1H-indazole 5-Bromo-3-iodo-1H-indazole

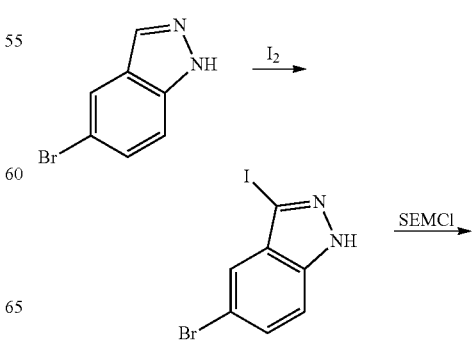

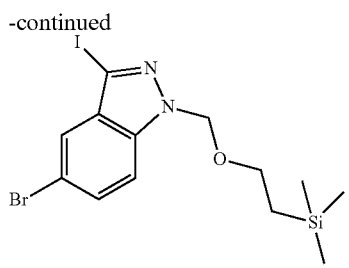

Step 1. 5-Bromo-3-iodo-1H-indazole

Into a round-bottom flask was dissolved 5-bromo-1H-indazole (1.99 g, 0.0101 mol) in N,N-dimethylformamide (10.0 mL). To this stirred solution was added potassium hydroxide (2.03 g, 0.0362 mol) then a cold solution of iodine (2.82 g, 0.0111 mol) in N,N-dimethylformamide (12.0 mL, 0.155 mol) was added dropwise. The mixture was stirred at room temperature for 2 hours before being added dropwise to an ammonium hydroxide (150 mL, 3.8 mol) solution in water (2.0 L) to give a precipitate. The precipitate was collected and dried under vacuum for 18 hours to yield 3.00 g (92%) of 5-bromo-3-iodo-1H-indazole.

$^1$H NMR (300 MHz, DMSO-d6): δ 13.681, s (br), 1H; 7.603, dd, J=1.2, 1.2 Hz, 1H; 7.550-7.527, m, 2H.
MS (ESI (+) m/z): 322.52/324.74 (M+H+).

Step 2: 5-Bromo-3-iodo-1-(2-trimethyisilanyl-ethoxymethyl)-1H-indazole and 5-Bromo-3-iodo-2-(2-trimethylsilanyl-ethoxymethyl)-1H-indazole Into a round-bottom flask was dissolved 5-bromo-3-iodo-1H-indazole (from Step 1, 3.00 g, 0.00929 mol) in tetrahydrofuran (25 mL, 0.31 mol; Acros). The mixture was cooled to 0° C. and sodium hydride (485 mg, 0.0121 mol) was added. Vigorous bubbling occurred. The mixture was then stirred for 10 minutes at room temperature before being cooled to 0° C. (β-(trimethylsilyl)ethoxy)methyl chloride (1.77 g, 0.0106 mol) was added dropwise and the mixture was stirred for 2 hours at room temperature. The reaction mixture was then diluted with ethyl acetate and washed with saturated sodium bicarbonate, and the organic phase dried over sodium sulfate. Silica gel was added to the solution, and the solvent removed under reduced pressure to produce silica gel loaded with the crude material. The silica gel was then loaded into ISCO solid-loading cartridges and purified by ISCO CombiFlash silica gel chromatography to yield two products identified as regioisomers 5-bromo-3-iodo-1-(2-trimethylsilanyl-ethoxymethyl)-1H-indazole and 5-bromo-3-iodo-2-(2-trimethylsilanyl-ethoxymethyl)-1H-indazole in a 3:1 mixture and 3.936 g (94%) overall yield. All subsequent reactions used this material as a mixture in varying ratios.

The high $R_f$ product was identified as 5-bromo-3-iodo-1-(2-trimethylsilanyl-ethoxymethyl)-1H-indazole by identification of the expected NOE interaction for the SEM methylene 1H to C-7 1H.

$^1$H NMR (300 MHz, DMSO-d6): δ 7.662, dd, J=0.6, 1.8 Hz, 1H; 7.551, dd, J=1.7, 8.8 Hz, 1H; 7.441, dd, J=0.6,8.8 Hz, 1H; 5.694, s, 2H; 3.546, dd, J=8.2, 8.2 Hz, 2H; 0.919-0.820, m, 2H; −0.061, s, 9H.
LCMS (m/z): 452.47/454.88 (M+H).
TLC $R_f$=0.67 in 3:1 hexanes/ethyl acetate.
The low $R_f$ product was identified as 5-bromo-3-iodo-2-(2-trimethylsilanyl-ethoxymethyl)-1H-indazole.

$^1$H NMR (300 MHz, DMSO-d6): δ 7.630, dd, J=0.7,1.8 Hz, 1H; 7.584, dd, J=0.8,9.2 Hz, 1H; 7.384, dd, J=1.9,9.2 Hz, 1H; 5.802, s, 2H; 3.640, dd; J=8.1,8.1 Hz, 2H; 0.983-0.811, m, 2H; −0.040, s, 9H.
LCMS (m/z): 452.50/454.49 (M+H).
TLC $R_f$=0.60 in 3:1 hexanes/ethyl acetate.

Example 1

3-(2-(5-bromo-1H-indazol-3-ylamino)-1H-benzo[d]imidazol-1-yl)propan-1-ol

Step 1: 1-(3-(tert-butyldimethylsilyloxy)propyl)-1H-benzo[d]imidazol-2-amine 1H-Benzoimidazol-2-ylamine (1 g, 7.5 mmol) was dissolved in acetone (30 mL) and powdered potassium hydroxide (2.12 g, 37.5 mmol) was added. The reaction was allowed to stir for several minutes at room temperature before (3-bromopropoxy)(tert-butyl)dimethylsilane (1.75 mL, 7.5 mmol) was added. After 1 hour, methylene chloride was added and the mixture was washed with water, brine and dried over magnesium sulfate. Upon concentration the crude product was dissolved in methylene chloride and purified by combiflash chromatography, methylene chloride to methylene chloride 6% MeOH gradient, to give 1-(3-(tert-butyldimethylsilyloxy)propyl)-1H-benzo[d]imidazol-2-amine (0.400 g, 1.3 mmol).
MS (ESI (+) m/z): 306.1 (M+H+)

Step 2: 5-bromo-1-(3-(tert-butyldimethylsilyloxy)propyl)-N-(1-(3-(tert-butyldimethylsilyloxy)propyl)-1H-benzonimidazol-2-yl)-1H-indazol-3-amine A mixture of 1-[3-(tert-butyl-dimethyl-silanyloxy)-propyl]-1H-benzoimidazol-2-ylamine (0.030 g, 0.0001 mol), 5-bromo-3-iodo-1-(2-trimethylsilanyl-ethoxymethyl)-1H-indazole (0.054 g, 0.00012 mol), xantphos (0.014 g, 0.00001 mol), tris-(dibenzylideneacetone)dipalladium(0) (0.009 g, 0.00001 mol), and potassium t-butoxide (0.017 g, 0.00015 mol) in toluene (1.0 mL) was degassed then subjected to microwave irradiation at 130° C. for 15 minutes. The mixture was dissolved in DMSO and purified by prepatory HPLC. The product fractions were concentrated and then again subjected to HPLC purification to give the title compound. These HPLC conditions resulted in removal of the silyl protecting groups.

$^1$H NMR (300 MHz, DMSO-d6): δ 13.14, s, 1H; 8.15, s, 1H; 7.62, m, 1H; 7.58-7.52, m, 3H; 7.33, m, 2H; 4.43, m, 2H; 3.54, m, 2H; 2.01, m, 2H.
MS (ESI (+) m/z): 385.75 (M+H+)

Example 2

3-{2-[5-(4-Methoxy-pyridin-3-yl)-1H-indazol-3-ylamino]-benioimidazol-1-yl}-propan-1-ol

Step 1: 5-bromo-N-(1-(3-(tert-butyldimethylsilyloxy)propyl)-1H-benzo[d]imidazol-2-yl)-1-((2-(trimethylsilyl)ethoxy)methyl)-1H-indazol-3-amine A mixture of 1-[3-(tert-butyldimethylsilyloxy)propyl]-1H-benzoimidazol-2-ylamine (0.400 g, 0.00131 mol), 5-bromo-3-iodo-1-((2-(trimethylsilyl)ethoxy)methyl)-1H-indazole (0.71 g, 0.0016 mol), xantphos (0.18 g, 0.00031 mol), tris-(dibenzylideneacetone)dipalladium(0) (0.120 g, 0.000131 mol), and potassium phosphate (0.42 g, 0.0020 mol) in 1,4-dioxane (3.0 mL) was degassed and subjected to microwave irradiation at 130° C. for 15 minutes. The mixture was filtered, concentrated and the residue dissolved in methylene chloride for purification by combiflash. A 40 g column was used along with a 10 to 40% gradient in ethyl acetate in hexane. The product fractions were concentrated to give 191 mg of the title compound.

MS (ESI (+)m/z) 629.94 (M+H+)

Step 2: N-(1-(3-(tert-butyldimethylsilyloxy)propyl)-1H-benzo[d]imidazol-2-yl)-5-(4-methoxypyridin-3-yl)-1-((2-(trimethylsilyl)ethoxy)methyl)-1H-indazol-3-amine A mixture of 5-bromo-N-(1-(3-(tert-butyldimethylsilyloxy)propyl)-1H-benzo[d]imidazol-2-yl)-1-((2-(trimethylsilyl)ethoxy)methyl)-1H-indazol-3-amine (from Step 1: 191 mg, 0.000303 mol), 4-methoxypyridin-3-yl-3-boronic acid (64 mg, 0.00042 mol) and (1,1'-bis(diphenylphosphino)-ferrocene)dichloropalladium(II), complexed with dichloromethane (1:1) (41 mg, 0.000050 mol), was dissolved in 1,4-dioxane (3.04 mL). To this mixture was added 2.0 M sodium carbonate in water (0.76 mL) with stirring. The mixture was flushed with argon sealed and heated at 110° C. After 3 hours, the mixture was diluted with methylene chloride, washed with water and brine, the organic phase dried over magnesium sulfate, filtered, and concentrated. The residue was dissolved in methylene chloride and purified by flash chromatography (50-100% ethyl acetate-0.3% triethylamine in hexanes) to give 132 mg (66%) of the title compound.

MS (ESI (+)m/z): 659.01 (M+H$^+$)

Step 3: 3-(2-(5-(4-methoxypyridin-3-yl)-1H-indazol-3-ylamino)-1H-benzo[d]imidazol-1-yl)propan-1-ol To a solution of {1-[3-(tert-butyl-dimethyl-silanyloxy)-propyl]-1H-benzoimidazol-2-yl}-[5-(4-methoxy-pyridin-3-yl)-1-(2-trimethylsilanyl-ethoxymethyl)-1H-indazol-3-yl]-amine (132 mg, 0.000200 mol) in ethanol (12.0 mL) was added 12 M HCl (4.0 mL) and the mixture was heated at reflux for 1 hour. The mixture was evaporated to dryness, the residue taken up in DMSO and purified by preparative HPLC to yield the title compound as the TFA salt.

$^1$H NMR (300 MHz, DMSO-d6): δ 13.27, s, 1H; 8.82, d, 1H J=7 Hz; 8.73, s, 1H, 8.24, s, 1H; 7.69, m, 4H; 7.59, d, 1H J=7 Hz; 7.37, m, 2H; 4.57, m, 2H; 4.08, s, 3H; 3.56; d, 2H, J=6 Hz; 2.02, m, 1H.

MS (ESI (+)m/)z 414.90 (M+H$^+$)

Example 3

(2-(5-(4-methoxypyridin-3-yl)-1H-indazol-3-ylamino)-1-phenyl-1H-benzo[d]imidazol-5-yl)methanol

Step 1: ((3-Nitro-4-(phenylamino)phenyl)methanol (4-Fluoro-3-nitrophenyl)methanol (1.500 g, 0.008765 mol), N,N-diisopropylethylamine (3.054 mL, 0.01753 mol), N,N-dimethylformamide (3.688 mL, 0.04764 mol), and aniline (2.40 mL, 0.0263 mol) were placed into three separate microwave vials. Each was reacted at 150° C. for 30 minutes. The resultant gel was dissolved in ethyl acetate, washed once with 5% citric acid and once with brine, dried and concentrated. The residue was used directly in the next step.

MS (ESI (+)m/z): 245.1 (M+H$^+$)

Step 2: ((3-amino-4-(phenylamino)phenyl)methanol ((3-Nitro-4-(phenylamino)phenyl)methanol (2.141 g, 0.008766 mol) was dissolved in methanol (40 mL) under a nitrogen atmosphere and 10% palladium on carbon (1:9, palladium:carbon black, 0.500 g) was added. The mixture was stirred under one atmosphere of hydrogen for 3 hours. The reaction was filtered, concentrated and the residue dissolved in ethyl acetate, washed with saturated sodium bicarbonate, dried over magnesium sulfate and concentrated to give a crude product that was used directly in the next step.

MS (EST (+)m/z): 215.3 (M+H$^+$)

Step 3: (2-amino-1-phenyl-1H-benzold[d]imidazol-5-yl)methanol

5 M Cyanogen bromide in acetonitrile (2.63 mL) was added to water (100 mL) and (3-amino-4-(phenylamino)phenyl)methanol (1.878 g, 0.008765 mol) in methanol (200 mL) was added dropwise to the solution of cyanogen bromide over 1 hour. The reaction was allowed to stir overnight then concentrated. The residue was dissolved in ethyl acetate, washed with saturated bicarbonate, brine, dried over magnesium sulfate and concentrated. The resultant residue was purified by flash chromatography using 6% methanol in DCM to give 450 mg of final product.

MS (ESI (+)m/z): 240.1 (M+H+)

Step 4: (2-(5-bromo-1((2-(trimethylsilyl)ethoxy)methyl)-1H-indazol-3-ylamino)-1-phenyl-1H-benzo[d]imidazol-5-yl)methanol A mixture of 5-bromo-3-iodo-1-((2-(trimethylsilyl)ethoxy)methyl)-1H-indazole (906 mg, 0.00200 mol), (2-amino-1-phenyl-1H-benzoimidazol-5-yl)methanol (435 mg, 0.00182 mol), copper(I) iodide (110 mg, 0.00056 mol), trans-N$^1$,N$^2$-dimethylcyclohexane-1,2-diamine (160 mg, 0.0011 mol) and potassium phosphate (772 mg, 0.00364 mol) in tetrahydrofuran (19.4 mL) was stirred under argon sparging until a greenish suspension formed. The mixture was then microwaved at 140° C. for 3 hours. The reaction mixture was diluted with ethyl acetate and washed with 5% citric acid, saturated sodium bicarbonate, brine, dried over magnesium sulfate and concentrated. The residue was purified by flash chromatography using 0-100% ethyl acetate-hexanes. The product was taken up in ethyl acetate, washed with 1N HCl to remove residual copper and rechromatograped to give 75 mg of product.

MS (ESI (+)m/z): 564.3 (M+H+)

Step 5: (2-(5-(4-methoxypyridin-3-yl)-1-((2-(trimethylsilypetboxy)methyl)-1H-indazol-3-ylamino)-1-phenyl-1H-benzo[d]imidazol-5-yl)methanol To a mixture of (2-(5-bromo-1-((2-(trimethylsilyl)ethoxy)methyl)-1H-indazol-3-ylamino)-1-phenyl-1H-benzo[d]imidazol-5-yl)methanol (74 mg, 0.00013 mol), 4-methoxypyridin-3-ylboronic acid (28 mg, 0.00018 mol), and [1,1'-bis(diphenylphosphino)ferrocene]-dichloropalladium(II), complex with dichloromethane (1:1) (18 mg, 0.000022 mol), in 1,4-dioxane (1.32 mL, 0.0169 mol) was added 2.0 M sodium carbonate in water (0.3 mL) with stirring. The reaction was flushed under an atmosphere of argon, sealed, and kept at 100° C. for 12-14 hours. The mixture was then cooled, diluted with ethyl acetate, washed with saturated sodium bicarbonate, brine, dried over magnesium sulfate and concentrated. The residue was taken up in methylene chloride and purified by ISCO CombiFlash silica gel chromatography, in 0-100% 0.2% ammonium hydroxide in ethyl acetate/hexanes to give 24 mg of the title compound.
MS (ESI (+)m/z): 593.2 (M+H$^+$).

Step 6: (2-(5-(4-methoxypyridin-3-yl)-1H-indazol-3-ylamino)-1-phenyl-1H-benzo[d]imidazol-5-yl)methanol A mixture of (2-(5-(4-methoxypyridin-3-yl)-1-((2-(trimethylsilyl)ethoxy)methyl)-1H-indazol-3-ylamino)-1-phenyl-1H-benzo[d]imidazol-5-yl)methanol (0.024 g, 0.000040 mol) and 0.03 M HCl (1 mL,) in ethanol (3 mL) was heated at 100° C. for 2 hours. The reaction was concentrated and the residue was dissolved in DMSO and purified by HPLC.
$^1$H NMR (300 MHz, DMSO-d6) δ: 13.20, s, 1H; 8.79, d, 1H J=7 Hz; 8.66, s, 1H, 8.24, s, 1H; 7.97, s, 1H; 7.81, m, 2H; 7.76-7.53, m, 6H; 7.21, m, 1H; 7.01, d, 1H, J=8 Hz; 4.59, s, 2H; 4.05, s, 3H.
MS (ESI (+) m/z): 463.61 (M+H+).

Example 4

Ethyl 1-(trans-4-hydroxycyclohexyl)-2-(5-(4-methoxypyridin-3-yl)-1H-indazol-3-ylamino)-1H-benzo[d]imidazole-5-carboxylate

Step 1: Ethyl 4-fluoro-3-nitrobenzoate

4-Fluoro-3-nitrobenzoic acid (5.3 g, 0.029 mol), ethanol (15 mL, 0.26 mol), toluene (40 mL, 0.4 mol) and sulfuric acid (1.75 mL, 0.0328 mol) were added to a 100 mL round-bottomed flask fitted with a Dean Stark trap and reflux condenser. The reaction mixture was heated with stirring under nitrogen to reflux and maintained at reflux for 5 hours. The reaction mixture was concentrated to about half volume diluted with ethyl acetate. The organic layer was washed with saturated sodium bicarbonate, water and dried over sodium sulfate. Concentration yielded a straw colored oil (5.68 g, 93%), which was used in the next step without further purification.

Step 2: Ethyl-(trans-4-hydroxycyclohexylamino)-3-nitrobenzoate

A mixture of ethyl 4-fluoro-3-nitrobenzoate (5.18 g, 0.0243 mol), trans-4-aminocyclohexanol (3.1 g, 0.027 mol), and N,N-diisopropylethylamine (12.5 mL, 0.0718 mol) in N,N-dimethylformamide (25 mL) in three 20-mL microwave reaction vessels was microwaved at 130° C. for 7 minutes. The combined mixtures were diluted with ethyl acetate, washed with 5% aqueous citric acid, brine, dried over sodium sulfate and concentrated to give 7.94 g of a yellow solid.
MS (ESI (+)m/z): 308.8 (M+H$^+$)

Step 3: Ethyl 3-amino-4-(trans-4-hydroxycyclohexylamino)benzoate

Ethyl-(trans-4-hydroxycyclohexylamino)-3-nitrobenzoate (1.04 g, 0.00337 mol) was dissolved in 15 mL of ethanol. The solution was sparged with nitrogen followed by the addition of 5% palladium on activated carbon. The reaction was stirred under 50 lbs of hydrogen until the uptake of hydrogen ceased. The reaction mixture was filtered through celite and concentrated to an off white solid (0.91 g, 97%).
MS (ESI (+)m/z): 278.56 (M+H$^+$)

Step 4: Ethyl 2-amino-1-(trans-4-hydroxycyclohexyl)-1H-benzimidazole-5-carboxylate 5.0 M cyanogen bromide in acetonitrile (1.0 mL) was added to water (35 mL) in a 250 mL round-bottom flask at room temperature with stirring. To this was added dropwise via an addition funnel ethyl 3-amino-4-(trans-4-hydroxycyclohexylamino)benzoate (0.91 g, 0.0033 mol) in methanol (70 mL) over 1 hour. After 3 hours the reaction mixture was concentrated to an off white residue. The residue was triturated with ethyl acetate and dried overnight in vacuo to give the title compound (0.97 g, 98%) as an off white solid.
MS (ESI (+)m/z): 303.75 (M+H$^+$)

Step 5: Ethyl 2-amino-1-(trans-4-(tert-butyldimethylsilyloxy)cyclohexyl)-1H-benzo[d]imidazole-5-carboxylate Ethyl 2-amino-1-(trans-4-hydroxycyclohexyl)-1H-benzimidazole-5-carboxylate (0.97 g, 0.0032 mol) was dissolved in N,N-dimethylformamide (10 mL, 0.2 mol) at room temperature. 1H-Imidazole (0.50 g, 0.0074 mol) and tert-butyldimethylsilyl chloride (0.53 g, 0.0035 mol) were added and the mixture stirred at room temperature for 1 hour. The reaction mixture was diluted with ethyl acetate and washed with saturated bicarbonate then brine. The organics were collected and dried over sodium sulfate and concentrated. The crude solid was purified by combiflash chromatography using methylene chloride and methanol as eluent. Product fractions were concentrated to give an off white solid (1.099 g). MS (ESI (+)m/z) 418.04 (M+H$^+$)

Step 6: Ethyl 2-(5-bromo-1-((2-(trimethylsilyl)ethoxy)methyl)-1H-indazol-3-ylamino)-1-(trans-4-(tert-butyldimethylsilyloxy)cyclohexyl)-1H-benzo[d]imidazole-5-carboxylate A mixture of ethyl 2-amino-1-(trans-4-(tert-butyldimethylsilyloxy)cyclohexyl)-1H-benzo[d]imidazole-5-carboxylate (102 mg, 0.000244 mol), 5-bromo-3-iodo-1-((2-(trimethylsilyl)ethoxy)methyl)-1H-indazole (130 mg, 0.00029 mol), 1,4-dioxane (0.6 mL, 0.007 mol), potassium phosphate (78 mg, 0.00037 mol), xantphos (34 mg, 0.000059 mol) and tris(dibenzylideneacetone)dipalladium(0) (20 mg, 0.00002 mol) was placed in a microwave reaction vessel. The reaction mixture was stirred under nitrogen and the sides were washed down with additional 1,4-dioxane (0.5 mL). The reaction vessel was irradiated under microwave radiation for 60 minutes at 130° C. The reaction mixture was diluted with ethyl acetate and washed with aqueous saturated sodium bicarbonate and then brine. The organic phase was dried over sodium sulfate and concentrated to a brown residue which was purified by combiflash chromatography on a 40 g silica gel cartridge using an initial eluent of 10% ethyl acetate-90% hexanes for 5 minutes then a gradient to 30% ethyl acetate over the next 15 minutes. Concentration of the product fractions gave a yellow oil (99.1 mg).
MS (ESI (+)m/z): 741.82 (M+H$^+$)

Step 7: Ethyl 1-((trans-4-(tert-butyldimethylsilyloxy)cyclohexyl)-2-(5-(4-methoxypyridin-3-yl)-1-((2-(trimethylsilyl)ethoxy)methyl)-1H-indazol-3-ylamino)-1H-benzo[d]imidazole-5-carboxylate Ethyl 2-(5-bromo-1-((2-(trimethylsilyl)ethoxy)methyl)-1H-indazol-3-ylamino)-1-(trans-4-(tert-butyldimethylsilyloxy)cyclohexyl)-1H-benzo[d]imidazole-5-carboxylate (90.1 mg, 0.000121 mol) and 4-methoxypyridin-3-yl-3-boronic acid (22 mg, 0.00014 mol) were added to a 20 mL vial and dissolved in 1,4-dioxane (2 mL, 0.02 mol). To the reaction mixture was added 2 M sodium carbonate in water (0.3 mL) followed by the addition of [1,1'-bis(diphenylphosphino)-ferrocene]dichloropalladium(II), complexed with dichloromethane (1:1) (10 mg, 0.00001 mol). The reaction mixture was heated under nitrogen at 90° C. for 1 hour. The reaction mixture was diluted with ethyl acetate, washed with saturated sodium bicarbonate solution and brine. The organic phase was dried over sodium sulfate and concentrated. The residue was purified by combiflash chromatography using methanol/methylene chloride as eluent and a 40 g silica gel cartridge. A gradient was run from 0% methanol to 4% methanol over 20 minutes. Concentrating the product fractions under high vacuum gave 56.8 mg of the title compound as a foam.

MS (ESI (+)m/z): 771.07 (M+H$^+$)

Step 8: Ethyl 1-(trans-4-hydroxycyclohexyl)-2-(5-(4-methoxypyridin-3-yl)-1H-indazol-3-ylamino)-1H-benzo[d]imidazole-5-carboxylate In a 20 mL vial ethyl 1-(trans-4-(tert-butyldimethylsilyloxy)cyclohexyl)-2-(5-(4-methoxypyridin-3-yl)-1-((2-(trimethylsilyl)ethoxy)methyl)-1H-indazol-3-ylamino)-1H-benzo[d]imidazole-5-carboxylate (25 mg, 0.000032 mol) was dissolved in ethanol (2 mL) and 12 M HCl (0.75 mL). The resultant mixture was heated at 100° C. for 1 hour before being concentrated to a pale yellow solid and purified by HPLC. The desired fractions were lyopholized to obtain the title compound as the TFA salt in a 62% yield.

$^1$H NMR (DMSO-d6, 300 MHz), δ 12.4(s,1H), 8.71(d, J=5.7 Hz, 2H), 7.78(d, J=5.9, 2H), 7.58-7.42(m, 5H), 4.97(t, 1H), 4.13(q, 2H), 4.01(s, 3H), 2.39(m, 2H), 1.94(d, J=9.9 Hz, 2H), 1.75(d, J=9.9 Hz, 2H), 1.36(m, 2H), 1.23(t, J=21 Hz, 3H).

MS (ESI (+)m/z): 527.05 (M+H+).

Example 5

N-(1-cyclohexyl-5-(morpholinomethyl)-1H-benzo[d]imidazol-2-yl)-5-(4-methoxypyridin-3-yl)-1H-indazol-3-amine Step 1: 4-Cyclohexylamino-3-nitrobenzoic acid, ethyl ester Ethyl 4-fluoro-3-nitrobenzoate (5.73 g, 0.0269 mol) was dissolved in 25 mL of DMF. While stirring under an atmosphere of nitrogen, cyclohexanamine in 5 mL of DMF (3.4 mL, 0.030 mol) and N,N-diisopropylethylamine (14 mL, 0.080 mol) were added simultaneously via two seperate syringes. The reaction mixture turned immediately into a deep yellow/orange gel and was diluted with another 5 mL of DMF. The reaction mixture was slightly exothermic and stirring was maintained until the reaction was complete as determined by LC/MS. The reaction mixture was then diluted with ethyl acetate and washed with 5% citric acid then brine. The organic phase was collected, dried over sodium sulfate and concentrated to a yellow oil which solidified under high vacuum to yield 8.47 g of the title compound.

MS (ESI (+)m/z): 292.63 (M+H$^+$).

Step 2: 3-Amino-4-cyclohexylaminobenzoic acid, ethyl ester

In a 250 mL round bottom flask ethyl 4-(cyclohexylamino)-3-nitrobenzoate (3.01 g, 0.0103 mol) was dissolved in ethanol (40 mL) and 1 gram of 5% palladium on carbon (54.62% water) was added. Cyclohexene (7 mL, 0.07 mol) was then added and the reaction heated at 83° C. for 3 hours. The reaction mixture was filtered through celite and the filter cake washed with ethanol. The combined filtrates were concentrated to give 2.3 g title compound as a brownish tan solid.

MS (ESI (+)m/z): 263.11 (M+H$^+$).

Step 3: Ethyl 2-amino-1-cyclohexyl-1H-benzo[d]imidazole-5-carboxylate

5 M cyanogen bromide in acetonitrile (2.25 mL) was added to water (25 mL, 1.4 mol) in a 250 mL round bottom flask at room temperature with stirring. To this was added dropwise a solution of 3-amino-4-cyclohexylaminobenzoic acid ethyl ester (2.25 g, 0.00858 mol) in ethanol (25 mL, 0.43 mol) via an additon funnel over 45 minutes. After 3 hours the reaction was concentrated. The residue was dissolved in ethyl acetate and washed with saturated sodium bicarbonate solution then brine. The organic phase was dried over sodium sulfate and concentrated to a dark solid. The solid was triturated with ethanol, filtered and washed with ethanol to give 1.747 g of the title compound as a grayish solid.

MS (ESI (+)m/z): 287.61 (M+H$^+$).

Step 4: (2-Amino-1-cyclohexyl-1H-benzimidazol-5-yl)methanol

In a 20 mL vial, ethyl 2-amino-1-cyclohexyl-1H-benzo[d]imidazole-5-carboxylate (101.5 mg, 0.0003532 mol) was dissoled in tetrahydrofuran (2 mL, 0.02 mol). While stirring under nitrogen, a solution of 1.0 M of lithium tetrahydroaluminate in tetrahydrofuran (1.0 mL) was added dropwise via a syringe to the reaction mixture. An initial reddish color occured followed by the reaction mixture becoming straw colored and a precipitate formed. After 1 hour the reaction was quenched by the dropwise addition of saturated ammonium chloride (1 mL). The mixture was extracted with ethyl acetate three times, the combined organic phases dried over sodium sulfate and concentrated to give the title compound (79.4 mg) as an off white solid.

MS (ESI (+) m/z): 245.68 (M+H$^+$)

Step 5: (2-(5-bromo-1-((2-(trimethylsilyl)ethoxy)methyl)-1H-indazol-3-ylamino)-1-cyclohexyl-1H-benzo[d]imidazol-5-yl)methanol In a 20 mL microwave reaction tube was weighed 5-bromo-3-iodo-1-((2-(trimethylsilyl)ethoxy)methyl)-1H-indazole (653 mg, 0.00144 mol). To this was added (2-amino-1-cyclohexyl-1H-benzoimidazol-5-yl)methanol (322.1 mg, 0.001313 mol), trans-N$^1$,N$^2$-dimethylcyclohexane-1,2-diamine (121 mg, 0.000851 mol), copper(I) iodide (78 mg, 0.00041 mol) and potassium phosphate (554 mg, 0.00261 mol). The tube was purged with argon and tetrahydrofuran (14 mL, 0.17 mol) was then added. The reaction mixture was stirred for several minutes with argon sparging at room temp. The reaction mixture was then heated under microwave irradiation for 5 hours at 140° C. The reaction mixture was cooled and diluted with ethyl acetate and washed twice with aqueous sodium bicarbonate, once with dilute HCl and one final wash with dilute sodium bicarbonate. The organic phase was dried over sodium sulfate and concentrated. The residue (750 mg) was purified by flash chromatography using a 120 g silica gel cartridge and hexane and ethyl acetate eluent. The product was loaded onto the column with methylene chloride and the eluent was initially 10% ethyl acetate for 2 minutes then a gradient to 60% ethyl acetate over 20 mins. The product fractions were combined and concentrated to yield 334.6 mg of a pale greenish white solid.

MS (ESI (+)m/z): 570.27 (M+H⁺)

Step 6: (1-cyclohexyl-2-(5-(4-methoxypyridin-3-yl)-1-((2-(trimethylsilyl)ethoxy)methyl)-1H-indazol-3-ylamino)-1H-benzo[d]imidazol-5-yl)methanol In a small microwave tube was added (2-(5-bromo-1-((2-(trimethylsilyl)ethoxy)methyl)-1H-indazol-3-ylamino)-1-cyclohexyl-1H-benzo[d]imidazol-5-yl)methanol (164 mg, 0.000287 mol), 4-methoxypyridin-3-ylboronic acid (79.1 mg, 0.000517 mol) and [1,1'-bis(diphenylphosphino)ferrocene]dichloropalladium(II),complex with dichloromethane (1:1) (47 mg, 0.000057 mol). To this mixture was added 1,4-dioxane (4.3 mL, 0.055 mol) and the resultant mixture was stirred under an argon atmosphere. To this mixture was then added 2 M sodium carbonate in water (700 uL) and the reaction mixture was microwaved for 21 minutes at 120° C. The reaction mixture filtered through a syringe filter cartridge and the cartridge washed 3 times with methanol. The residue after concentration was purified by flash chromatography using a 40 g silica gel cartridge and 10-60% ethyl acetate/hexane gradient. The product fractions were concentrated to give the title compound (29 mg).

MS (ESI (+)m/z): 598.83 (M+H⁺).

Step 7: 1-cyclohexyl-2-(5-(4-methoxypyridin-3-yl)-1-((2-(trimethylsilyl)ethoxy)methyl)-1H-indazol-3-ylamino)-1H-benzo[d]imidazole-5-carbaldehyde In a 20 mL vial was added (2-(1-((2-(trimethylsilyl)ethoxy)methyl)-5-(4-methoxypyridin-3-yl)-1H-indazol-3-ylamino)-1-cyclohexyl-1H-benzo[d]midazol-5-yl)methanol (29 mg, 0.048 mmol.) and 2 mL of methylene chloride. The reaction mixture was cooled in an ice water bath followed by the addition of Dess-Martin periodinane (29 mg, 0.68 mmol.). After 1 hour, the reaction mixture was diluted with methylene chloride, washed with aqueous sodium sulfite, and aqueous saturated sodium bicarbonate solution. The organic phase was dried over sodium sulfate and concentrated to a brown residue (28 mg) which was used directly in the next step.

MS (ESI (+)m/z): 596.94 (M+H⁺).

Step 8: N-(1-cyclohexyl-5-(morpholinomethyl)-1H-benzo[d]imidazol-2-yl)-5-(4-methoxypyridin-3-yl)-1-((2-(trimethylsilyl)ethoxy)methyl)-1H-indazol-3-amine In a 20 mL vial was added 1-cyclohexyl-2-(5-(4-methoxypyridin-3-yl)-1-((2-(trimethylsilyl)ethoxy)methyl)-1H-indazol-3-ylamino)-1H-benzo[d]imidazole-5-carbaldehyde (28 mg, 0.047 mmol.), morpholine (10 mg, 0.11 mmol) and methylene chloride (2 mL). A catalytic amount of acetic acid was added and the reaction mixture stirred at room temperature for 10 min. Sodium triacetoxyborohydride (30 mg, 0.14 mmol) was then added and the reaction mixture stirred at room temperature overnight. The reaction mixture was diluted with methylene chloride and washed with water, saturated sodium bicarbonate and brine. The organic layer was dried over sodium sulfate and concentrated to give the title compound (15 mg) which was used directly in the next step.

MS (ESI (+)m/z): 668.12 (M+H⁺).

Step 9: N-(1-cyclohexyl-5-(morpholinomethyl)-1H-benzo[d]imidazol-2-yl)-5-(4-methoxypyridin-3-yl)-1H-indazol-3-amine A mixture of (1-cyclohexyl-5-morpholin-4-ylmethyl-1H-benzoimidazol-2-yl)-[5-(4-methoxy-pyridin-3-yl)-1-(2-trimethylsilanyl-ethoxymethyl)-1H-indazol-3-yl]-amine (15 mg, 0.000022 mol), hydrogen chloride (300 uL, 0.01 mol) and ethanol (1.2 mL, 0.020 mol) in a 5 mL test tube with a septum cover was heated at 78° C. for 2 hours. The reaction mixture was concentrated and purified by HPLC to yield 1.5 mg after lyopholizaion.

MS (ESI (+)m/z): 538.52 (M+H⁺).

Example 6

Ethyl 1-(1-(trans-4-hydroxycyclohexyl)-2-(5-(4-methoxypyridin-3-yl)-1H-indazol-3-ylamino)-1H-benzo[d]imidazol-5-yl)methyl)piperidine-4-carboxylate Step 1: Ethyl 1-((1-(trans-4-(tert-butyldimethylsilyloxy)cyclohexyl)-2-(5-(4-methoxypyridin-3-yl)-1-((2-(trimethylsilyl)ethoxy)methyl)-1H-indazol-3-ylamino)-1H-benzo[d]imidazol-5-yl)methyl)piperidine-4-carboxylate To a 20 mL vial was added 1-((4-trans-(tert-butyldimethylsilyloxy)cyclohexyl)-2-(5-(4-methoxypyridin-3-yl))-1-((2-(trimethylsilyl)ethoxy)methyl)-1H-indazol-3-ylamino)-1H-benzo[d]imidazole-5-carbaldehyde ((36 mg, 0.000050 mol, prepared as in Example 7, step 7, from the corresponding alcohol and used directly; MS (ESI (+)m/z): 727.46 (M+H⁺)), ethyl piperidine-4-carboxylate (12 mg, 0.000074 mol) and methylene chloride (2 mL, 0.03 mol). To this mixture was added acetic acid (100 uL, 0.002 mol) and the reaction mixture was stirred at room temperature for 5 minutes. Sodium triacetoxyborohydride (31 mg, 0.00015 mol) was then added and the reaction stirred overnight at room temperature. After this time the reaction was diluted with methylene chloride and washed with water, aqueous saturated sodium bicarbonate and brine, dried over sodium sulfate and concentrated to give the title compound (38 mg) which was used directly in the next step.

MS (ESI (+)m/z): 869.45 (M+H+)

Step 2: Ethyl 1-(1-(trans-4-hydroxycyclohexyl)-2-(5-(4-methoxypyridin-3-yl)-1H-indazol-3-ylamino)-1H-benzo[d]imidazol-5-yl)methyl)piperidine-4-carboxylate In a 20 mL vial was added ethyl 1-((1-(trans-4-(tert-butyldimethylsilyloxy)cyclohexyl)-2-(5-(4-methoxypyridin-3-yl)-1-((2-(trimethylsilyl)ethoxy)methyl)-1H-1-indazol-3-ylamino)-1H-benzo(d)imidazol-5-yl)methyl)piperidine-4-carboxylat. (30 mg, 0.00003 mol), ethanol (1.20 mL, 0.0206 mol) and hydrogen chloride (300 uL, 0.01M). The mixture was brought to reflux and maintained at reflux for 1 hour. The reaction mixture was concentrated to a brownish residue and purified directly by HPLC yielding after lyopholization of the product fractions 4.5 mg of the title compound as a white solid as the bis TFA salt.

¹H NMR (DMSO-d6, 300 MHz) δ 12.92 (broad s, 1H), 9.71 (broad s, 1H), 8.70 (m, 2H), 7.96 (s, 1H), 7.73-7.44 (m, 5H), 7.27 (m, 1H), 4.70 (m, 1H), 4.31 (s, 2H), 3.97 (m, 5H), 3.33 (m, 1H), 2.82 (m, 1H), 2.44 (m, 1H), 2.47-2.30 (m, 9H), 2.01-1.67 (m, 8H), and 1.3-1.0 (m, 2H)

MS (ESI (+)m/z): 624.39 (M+H⁺). .

Example 7

4-(2-(5-(4-methoxypyridin-3-yl)-1H-indazol-3-ylamino)-5-((4-(2-(pyridin-4-yl)ethyl)piperazin-1-yl)methyl)-1H-benzo[d]imidazol-1-yl)cyclohexanol Step 1: N-(1-(4-(tert-butyldimethylsilyloxy)cyclohexyl)-5-((4-(2-(pyridin-4-yl)ethyl)piperazin-1-yl)methyl)-1H-benzo[d]imidazol-2-yl)-5-(4-methoxypyridin-3-yl)-1-((2-(trimethylsilyl)ethoxy)methyl)-1H-indazol-3-amine In a 20 mL vial was added 1-cyclohexyl-2-(5-(4-methoxypyridin-3-yl)-1-((2-(trimethylsilyl)ethoxy)methyl)-1H-indazol-3-ylamino)-1H-benzo[d]imidazole-5-carbaldehyde (36 mg, 0.000050 mol), 1-(2-(pyridin-4-yl)ethyl)piperazine (14 mg, 0.000074 mol) and methylene chloride (2 mL, 0.03 mol). To this mixture was added acetic acid (100 uL, 0.002 mol) followed by 5 minutes of stirring then addition of sodium triacetoxyborohydride (31 mg, 0.00015 mol). The reaction was allowed to proceed overnight at room temperature. The reaction mixture was diluted with methylene chloride, washed with water, aqueous saturated sodium bicarbonate and brine, dried over sodium sulfate and concentrated to 33 mg of title compound which was used directly in the next step.
MS (ESI (+)m/z): 903.57 (M+H+)

Step 2: (trans)-4-(2-(5-(4-methoxypyridin-3-yl)-1H-indazol-3-ylamino)-5(4-(2-(pyridin-4-yl)ethyl)piperazin-1-yl)methyl)-1H-benzo[d]imidazol-1-yl)cyclohexanol In a 20 mL vial was added N-(1-(4-(tert-butyldimethylsilyloxy)cyclohexyl)-5-((4-(2-(pyridin-4-yl)ethyl)piperazin-1-yl)methyl)-1H-benzo[d]imidazol-2-yl)-5-(4-methoxypyridin-3-yl)-1-((2-(trimethylsilyl)ethoxy)methyl)-1H-indazol-3-amine (31 mg, 0.000034 mol) ethanol (1.20 mL) and 0.01M hydrogen chloride (300 uL). The reaction mixture was brought to reflux and maintained at reflux for 1 hour. The reaction mixture was concentrated to a brownish residue and purified by HPLC yielding 8.3 mg of the title compound as the bis TFA salt as a white solid.
$^1$H NMR (DMSO-d6, 300 MHz): δ 12.90 (broad s, 1H), 8.77 (m, 1H), 8.69 (m, 3H), 7.98 (s, 1H), 7.59-7.27 (m, 8H), 7.19 (m, 1H), 4.69 (m, 1H), 4.01 (m, 5H), 3.66 (m, 1H), 2.80 (m, 4H), 2.47-2.20 (m, 11H), 2.20-1.92 (m, 4H), 1.36 (m, 2H).
MS (ESI (+)m/z): 658.54 (M+H+).

Example 8

(1-cyclohexyl-2-(5-(3-(methoxymethyl)phenyl)-1H-indazol-3-ylamino)-1H-benzo[d]imidazol-5-yl)methanol Step 1: (1-cyclohexyl-2-(5-(3-(methoxymethyl)phenyl)-1-((2-(trimethylsilyl)ethoxy)methyl)-1H-indazol-3-ylamino)-1H-benzo[d]imidazol-5-yl)methanol In a small microwave tube added (2-(5-bromo-1-((2-(trimethylsilyl)ethoxy)methyl)-1H-indazol-3-ylamino)-1-cyclohexyl-1H-benzo[d]imidazol-5-yl)methanol (52.4 mg, 0.0000918 mol), 3-(methoxymethyl)phenylboronic acid (25.1 mg, 0.000151 mol) and (1,1'-bis(diphenylphosphino)ferrocene)dichloropalladium(II) complexed with dichloromethane (1:1) (16.2 mg, 0.0000198 mol). The tube was flushed with argon and the contents were dissolved in 1,4-dioxane (1.5 mL) and 2 M sodium carbonate (150 uL). The reaction was microwaved for 10 minutes at 120° C. The cooled reaction mixture was filtered through a syringe filter and the filter washed 3× with methanol. The combined eluents were concentrated to yield 58 mg of crude product used directly in the next step.
MS (ESI (+)m/z): 612.36 (M+H+).

Step 2: {1-Cyclohexyl-2-[5-(3-methoxymethyl-phenyl)-1H-indazol-3-ylamino]-1H-benzoimidazol-5-yl}-methanol In a 20 mL vial with septum cover was added {1-cyclohexyl-2-[5-(3-methoxymethyl-phenyl)-1-(2-trimethylsilanyl-ethoxymethyl)-1H-indazol-3-ylamino]-1H-benzoimidazol-5-yl}-methanol (58 mg, 0.000095 mol), ethanol (6.0 mL) and HCl (2.0 mL, 0.065 M). The mixture was refluxed for 1.5 hr. The mixture was concentrated and the residue dissolved in approx 1.5 mL of DMSO and purified by HPLC. The product fractions were lyophilized overnight to give 11.9 mg of the title compound as an off white solid.
$^1$H NMR (DMSO-d6, 300 MHz) δ: 11.28 (broad s, 1H), 9.17 (broad s, 1H), 8.19 (s, 1H), 7.65 (m, 3H), 7.47-7.06 (m, 6H), 4.92 (m, 1H), 4.84 (s, 1H), 3.49 (s, 3H), 2.22 (m, 1H), 1.97 (m, 2H), 1.35 (m, 2H), 1.24 (m, 6H), 0.94 (m, 4H).
MS (ESI (+)m/z): 482.30 (M+H+)

Example 9

(2-(5-(3-aminophenyl)-1H-indazol-3-ylamino)-1-cyclohexyl-1H-benzo[d]imidazol-5-yl)methanol The title compound was prepared using the methods described in Example 8, but substituting 3-aminophenylboronic acid for 3-methoxymethylphenylboronic acid.
$^1$H NMR (MeOD-d4, 300 MHz) δ 8.19 (s, 1H), 7.78-7.70 (m, 2H), 7.62-7.30 (m, 6H), 7.14 (d, J=6.9 Hz, 1H), 4.63 (s, 2H), 3.25 (m, 1H), 2.38-2.27 (m, 3H), 2.06-1.19 (m, 9H).
MS (ESI (+) m/z): 453.33 (M+H+)

Example 10

2-(5-(2-methoxyphenyl)-1H-indazol-3-ylamino)-N-cyclopentyl-1-(trans-4-hydroxycyclohexyl)-1H-benzo[d]imidazole-5-carboxamide Step 1: 2-(5-bromo-1((2-(trimethylsilyl)ethoxy)methyl)-1H-indazol-3-ylamino)-1-(4-(tert-butyldimethylsilyloxy)cyclohexyl)-1H-benzoldimidazole-5-carboxylic acid A mixture of ethyl 2-(5-bromo-1-((2-(trimethylsilyl)ethoxy)methyl)-1H-indazol-3-ylamino)-1-(4-(tert-butyldimethylsilyloxy)cyclohexyl)-1H-benzo[d]imidazole-5-carboxylate (212.9 mg, 0.0002866 mol), and 1N potassium hydroxide in methanol (10.0 mL) was heated at 80° C. for 6 hr. The cooled reaction mixture was diulueted with ethyl acetate (60 mL), washed with 60 mL of 1N HCl, 60 mL of water, and 60 mL of brine, dried over magnesium sulfate and concentrated. Purification was performed by chromatography on silica using 20-35% EtOAc/Hexanes (+1% AcOH).
MS (ESI (+)m/z): 714.28 and 716.28 (M+H+)

Step 2: 2-[5-Bromo-1-(2-trimethylsilanyl-ethoxymethyl)-1H-indazol-3-ylamino]-1-[4-(tert-butyl-dimethyl-silanyloxy)-cyclohexyl]-1H-benzoimidazole-5-carboxylic acid cyclopentylamide N,N-Diisopropylethylamine (19.6 uL, 0.000112 mol) was added to a solution of 2-(5-bromo-1-((2-(trimethylsilyl)ethoxy)methyl)-1H-indazol-3-ylamino)-1-(4-(tert-butyldimethylsilyloxy)cyclohexyl)-1H-benzo[d]imidazole-5-carboxylic acid (26.8 mg, 0.0000375 mol), 2-chloro-1-methylpyridinium iodide (19.2 mg, 0.0000750 mol) and 1-hydroxybenzotriazole (10.1 mg, 0.0000750 mol) tetrahydrofuran (0.40 mL). The mixture was stirred at room temperature for 20 minutes. Cyclopentanamine (0.000112 mol) was then added and the mixture stirred for 2 hours. The mixture was diluted with ethyl acetate, washed with water, dried over magnesium sulfate and purified by flash chromatography.

MS (ESI (+)m/z): 781.46 and 783.48 (M+H+).

Step 3: 1-(4-(tert-butyldimethylsilyloxy)cyclohexyl)-N-cyclopentyl-2-(5-(2-methoxyphenyl)-1-((2-(trimethylsilyl)ethoxy)methyl)-1H-indazol-3-ylamino)-1H-benzo[d]imidazole-5-carboxamide A mixture of (1,1-Bis(diphenylphosphino)ferrocene)dichloropalladium(II), complexed with dichloromethane (1:1) (1.9 mg, 0.0000023 mol), 50 uL of 0.20 M 2-(5-bromo-1-(2-trimethylsilanyl-ethoxymethyl)-1H-indazol-3-ylamino)-1-(4-(tert-butyl-dimethyl-silanyloxy)-cyclohexyl)-1H-benzoimidazole-5-carboxylic acid cyclopentylamide (0.0000116 mol) in dioxane and 92 uL of 0.25 M 2-methoxyphenylboronic acid (3.54 mg, 0.0000233 mol) in dioxane and 29 uL 2.0 M sodium carbonate in water was heated at 120° C. for 4 hours. The reaction mixture was cooled, and 2 mL of H$_2$O was added followed by extraction with 2 mL of methylene chloride 3 times. The combined organic phases were concentrated and purified by flash chromatography with 50% EtOAc/Hexanes to give the title compound.

MS (ESI (+)m/z): 809.6 (M+H+).

Step 4: 2-(5-(2-methoxyphenyl)-1H-indazol-3-ylamino)-N-cyclopentyl-1-(trans-4-hydroxycyclohexyl)-1H-benzo[d]imidazole-5-carboxamide A mixture of 1-(4-(tert-butyldimethylsilyloxy)cyclohexyl)-N-cyclopentyl-2-(5-(2-methoxyphenyl)-1-((2-(trimethylsilyl)ethoxy)methyl)-1H-indazol-3-ylamino)-1H-benzo[d]imidazole-5-carboxamide (15 mg, 0.000018 mol), HCl (300 uL, 0.01 M) and ethanol (1.2 mL) was heated at reflux 78° C. for 2 hours. The mixture was concentrated and purified by HPLC. The product fractions were lyopholized to yield the title compound.

MS (ESI (+)m/z): 565.10 (M+H+).

Example 11

1-(4-Hydroxy-cyclohexyl)-2-[5-(2-trifluoromethoxy-phenyl)-1H-indazol-3-ylamino]-1H-benzoimidazole-5-carboxylic acid (3-methyl-butyl)-amide The title compound was obtained by following the methods and procedures described in Example 10 but substituting isopentylamine for cyclopentanamine and 2-trifluromethoxyphenylboronic acid for 2-methoxyphenylboronic acid.

MS (ESI (+)m/z): 621.48 (M+H+).

Example 12

1-(4-Hydroxy-cyclohexyl)-2-[5-(2-trifluoromethoxy-phenyl)-1H-indazol-3-ylamino]-1H-benzoimidazole-5-carboxylic acid cyclopentylamide The title compound was obtained by following the methods and procedures described in Example 10 but substituting 2-trifluromethoxyphenylboronic acid for 2-methoxyphenylboronic acid.

MS (ESI (+)m/z): 619.44 (M+H+).

Example 13

{1-(4-Hydroxy-cyclohexyl)-2-[5-(2-methoxy-phenyl)-1H-indazol-3-ylamino]-1H-benzoimidazol-5-yl}-pyrrolidin-1-yl-methanone The title compound was obtained by following the methods and procedures described in Example 10 but substituting pyrrolidine for cyclopentanamine.

MS (ESI (+) m/z): 551.55 (M+H+).

Example 14

1-(4-Hydroxy-cyclohexyl)-2-[5-(2-methoxy-phenyl)-1H-indazol-3-ylamino]-1H-benzoimidazole-5-carboxylic acid (3-methyl-butyl)-amide The title compound was obtained by following the methods and procedures described in Example 10 but substituting isopentylamine for cyclopentanamine.

MS (ESI (+)m/z): 567.27 (M+H+).

Example 15

N-(1-cyclohexyl-5-(piperidin-1-ylmethyl)-1H-benzo[d]imidazol-2-yl)-5-(4-methoxypyridin-3-yl)-1H-indazol-3-amine

Step 1: 1-(4-Fluoro-3-nitro-benzyl)-piperidine

4-Fluoro-3-nitro-benzaldehyde (3.39 g, 0.0200 mol) was dissolved in methylene chloride (100 mL) and acetic acid (3.50 mL, 0.0616 mol) and the mixture was cooled to −10° C. Piperidine (2.4 mL, 0.024 mol) was then added to the cooled mixture over 10 minutes. Sodium triacetoxyborohydride (17.0 g, 0.0802 mol) was added in one portion. After stirring at 0° C. for 18 hours, the reaction was poured into a mixture of 1N aqueous HCl and ice. The organic phase was removed, and the aqueous layer was made basic by the addition of NaOH pellets. The aqueous layer was extracted twice with methylene chloride, dried over magnesium sulfate, filtered and concentrated. The residue was taken up in methylene chloride and purified by silica gel chromatography (ethyl acetate/hexanes as eluent) followed by further purification by preparative HPLC to yield 2.69 g of 1-(4-fluoro-3-nitro-benzyl)-piperidine as a TFA salt.

$^1$H NMR (300 MHz, CDCl3) δ: 8.101, m, 1H; 7.902, m, 1H; 7.403, m, 1H; 7.243, m, 1H; 4.231, s, 2H; 3.583, m, 2H; 2.631, m, 2H; 2.082-1.794, m, 5H; 1.410, m, 1H

MS (ESI (+)m/z): 238.65 (M+H+).

Step 2: N-cyclohexyl-2-nitro-4-(piperidin-1-ylmethyl)aniline 1-(4-Fluoro-3-nitro-benzyl)-piperidine—TFA salt (2.69 g, 0.00764 mol), cyclohexanamine (3.87 mL, 0.0339 mol) and N,N-Diisopropylethylamine (6.00 mL, 0.0344 mol) were dissolved in N,N-dimethylformamide (8.00 mL, 0.103 mol). The mixture was apportioned into four vials and each was microwaved at 300 watts, 130° C. for 7 minutes. The combined reaction mixtures were diluted with ethyl acetate, washed with 5% citric acid, saturated sodium chloride, dried over sodium sulfate and concentrated to give 3.40 g of the title compound as the citrate salt.

MS (ESI (+) m/z): 317.95 (M+H+).

Step 3: $N^1$-cyclohexyl-4-(piperidin-1-ylmethyl)benzene-1,2-diamine

N-cyclohexyl-2-nitro-4-(piperidin-1-ylmethyl)aniline as the citrate salt (3.40 g, 0.00681 mol) was dissolved in ethanol (65 mL). To this was added 5% Pd/C (406 mg). The solution was flushed three times with hydrogen, then hydrogenated at atmospheric pressure under a balloon of hydrogen for 1 hour. The mixture was filtered and concentrated to dryness to yield $N^1$-cyclohexyl-4-(piperidin-1-ylmethyl)benzene-1,2-diamine used directly in the next step.

Step 4: 1-cyclohexyl-5-(piperidin-1-ylmethyl)-1H-benzo[d]imidazol-2-amine $N^1$-cyclohexyl-4-(piperidin-1-ylmethyl)benzene-1,2-diamine from step3 in methanol (200 mL) was added to a mixture of 5 M cyanogen bromide in acetonitrile (3.2 mL) and water (100 mL) dropwise over 1 hr with stirring. After 4.5 hr total reaction time, the mixture was evaporated to dryness. The residue was purified by preparative HPLC chromatography to yield 2.23 g of the title compound as the bis-TFA salt.

$^1$H NMR (300 MHz, CDCl3) δ: 11.300, s (br), 1H; 8.199, s (br), 2H; 7.551-7.401, m, 3H; 4.098, m, 1H; 3.577, m, 2H; 2.642, m, 2H; 2.197-1.769, 14H; 1.607-1.212, m, 3H.

MS (ESI (+)m/z): 312.90 (M+H+).

Step 5: 5-bromo-N-(1-cyclohexyl-5-(piperidin-1-ylmethyl)-1H-benzo[d]imidazol-2-yl)-1-((2-(trimethylsilyl)ethoxy)methyl)-1H-indazol-3-amine A mixture of 1-cyclohexyl-5-(piperidin-1-ylmethyl)-1H-benzo[d]imidazol-2-amine (420 mg, 0.00134 mol), 5-bromo-3-iodo-1-((2-(trimethylsilyl)ethoxy)methyl)-1H-indazole (916 mg, 0.00202 mol), xantphos (237 mg, 0.000410 mol), tris(dibenzylideneacetone)dipalladium(0) (147 mg, 0.000160 mol), and potassium phosphate (510 mg, 0.00240 mol) in 1,4-Dioxane (6.0 mL) was flushed with argon. The mixture was microwaved at 300 watts, 130° C. for 15 minutes. The reaction mixture was filtered, concentrated and purified by preparative HPLC to yield 582 mg of 5-bromo-N-(1-cyclohexyl-5-(piperidin-1-ylmethyl)-1H-benzo[d]imidazol-2-yl)-1-((2-(trimethylsilyl)ethoxy)methyl)-1H-indazol-3-amine as the bis-TFA salt.

$^1$H NMR (300 MHz, CDCl3) δ: 11.076, s (br), 1H; 8.145-6.680, m, 6H; 5.795-5.497, m, 2H; 4.211, m, 1H; 3.843-3.455, m, 4H; 2.889-2.555, m, 2H; 2.295-1.143, m, 20H; 1.048-0.817, m, 2H; −0.075, s, 9H.

MS (ESI (+) m/z): 636.90 (M+H+).

Step 6: N-(1-cyclohexyl-5-(piperidin-1-ylmethyl)-1H-benzo[d]imidazol-2-yl)-5-(4-methoxypyridin-3-yl)-1-((2-(trimethylsilyl)ethoxy)methyl)-1H-indazol-3-amine A mixture of 5-bromo-N-(1-cyclohexyl-5-(piperidin-1-ylmethyl)-1H-benzo[d]imidazol-2-yl)-1-((2-(trimethylsilyl)ethoxy)methyl)-1H-indazol-3-amine as bis-TFA salt (204 mg, 0.000235 mol), 4-methoxypyridin-3-yl-3-boronic acid (63 mg, 0.00041 mol), [1,1'-bis(diphenylphosphino)ferrocene]dichloropalladium(II),complex with dichloromethane (1:1) (27 mg, 0.000033 mol) and 0.75 mL 2.0 M sodium carbonate 1,4-Dioxane (3.0 mL) was flushed with argon and sealed. The mixture was heated at 110° C. for 3 hr, diluted with methylene chloride, washed with water, saturated sodium bicarbonate, dried over magnesium sulfate and concentrated to give N-(1-cyclohexyl-5-(piperidin-1-ylmethyl)-1H-benzo[d]imidazol-2-yl)-5-(4-methoxypyridin-3-yl)-1-((2-(trimethylsilyl)ethoxy)methyl)-1H-indazol-3-amine which was used directly in the next step.

Step 7: (1-Cyclohexyl-5-piperidin-1-ylmethyl-1H-benzoimidazol-2-yl)-[5-(4-methoxy-pyridin-3-yl)-1H-indazol-3-yl]-amine N-(1-cyclohexyl-5-(piperidin-1-ylmethyl)-1H-benzo[d]imidazol-2-yl)-5-(4-methoxypyridin-3-yl)-1-((2-(trimethylsilyl)ethoxy)methyl)-1H-indazol-3-amine (from Step 6) was dissolved in ethanol (6.0 mL). To this solution was added 12 M HCl (2.0 mL) and the mixture was heated at 100° C. for 1 hour. The mixture was evaporated to dryness and the residue purified by preparative HPLC to yield 36 mg (20% over 2 steps) of the title compound as the bis-TFA salt.

$^1$H NMR (300 MHz, DMSO-d6) δ: 9.266, s (br), 1H; 8.807-8.662, m, 2H; 7.944, s (br), 1H; 7.762-7.437, m, 5H; 7.261, m, 1H; 4.723, m, 1H; 4.310, m, 2H; 4.045, s, 3H; 3.399-3.251, m, 2H; 2.954-2.687, m, 2H; 2.482-2.186, m, 2H; 1.969-1.229, m, 15H.

LCMS m/z=536.09 M+H.

Example 16

(1-cyclohexyl-2-(5-(4-methoxypyridin-3-yl)-1H-indazol-3-ylamino)-1H-benzo[d]imidazol-5-yl) methanol

Step 1: (4-Cyclohexylamino-3-nitro-phenyl)methanol

A mixture of (4-Fluoro-3-nitrophenyl)methanol (1.00 g, 0.0058 mol), N,N-diisopropylethylamine (2.036 mL, 0.0117) and cyclohexanamine (2.005 mL, 0.0175 mol) in N,N-Dimethylformamide (2.46 mL) was placed in a microwave vial, the contents were mixed thoroughly then microwaved at 130° C. for 7 minutes. The resultant gel was dissolved in ethyl acetate then washed with 5% citric acid, brine, dried and concentrated to give the title compound.

Step 2: (3-Amino-4-(cyclohexylamino)phenyl)methanol

To (4-cyclohexylamino-3-nitro-phenyl)methanol (1.46 g, 0.0058 mol) in ethanol (35 mL, 0.6 mol) was added 5% Pd/C (0.20 g, 0.00009 mol). The mixture was flushed with hydrogen then stirred for 2 hr at room temperature under 1 atm of hydrogen. The reaction mixture was concentrated and the residue purified by flash chromatography with a gradient from 40 to 100 percent ethyl acetate in hexanes to provide 1.010 g the title compound.

MS (ESI (+)m/z): 220.48 (M+H+).

Step 3: (2-Amino-1-cyclohexyl-1H-benzoimidazol-5-yl)methanol

A solution of (3-amino-4-(cyclohexylamino)phenyl) methanol (1.010 g, 0.004584 mol) in methanol (100 mL) was added dropwise over 1 hr to a mixture of cyanogen bromide (1.4 mL, 0.5 M in acetonitrile) and water (50 mL). After 3 hours the mixture was concentrated and the residue purified by preparative HPLC using a 5 to 50% gradient over 20 min. Concentration of product fractions gave 1.117 g of the TFA salt of the title compound as a white powder.

MS (ESI (+)m/z): 245.75 (M+H+).

Step 4: 5-((tert-butyldimethylsilyloxy)methyl)-1-cyclohexyl-1H-benzo[d]imidazol-2-amine To a solution of (2-Amino-1-cyclohexyl-1H-benzoimidazol-5-yl)methanol (0.650 g, 0.00265 mol) and 1H-Imidazole (0.4149 g, 0.006094 mol) in N,N-Dimethylformamide (10 mL) was added tert-Butyldimethylsilyl chloride (0.4393 g, 0.002914 mol) and the mixture stirred for 1 hour. The mixture was diluted with ethyl acetate, washed with saturated socium bicarbonate, dried and concentrated. The residue was taken up in methylene chloride containing 0.1% triethylamine and purified by flash chromatography with a gradient of from 0 to 10 percent methanol. The product fractions were concentrated to give 539 mg of the product.

MS (ESI (+)m/z): 360.08 (M+H+).

Step 5: 5-Bromo-1-(2-trimethylsilanyl-ethoxymethyl)-1H-indazol-3-yl]-[5-(tert-butyl-dimethyl-silanyloxymethyl)-1-cyclohexyl-1H-benzoimidazol-2-yl]-amine A mixture of 5-((tert-butyldimethylsilyloxy)methyl)-1-cyclohexyl-1H-benzo[d]imidazol-2-amine (425 mg, 0.00118 mol), 5-bromo-3-iodo-1-((2-(trimethylsilyl)ethoxy)methyl)-1H-indazole (850 mg, 0.0019 mo), xantphos (169 mg, 0.000292 mol), tris(dibenzylideneacetone)-dipalladium(0) (132 mg, 0.000144 mol), and potassium phosphate (518 mg, 0.00244 mol) in 1,4-dioxane (6.0 mL) was microwaved at 300 watts, 130° C. for 15 minutes. The reaction mixture was filtered, concentrated, and purified by flash chromatography to yield 448 mg of the title compound.

$^1$H NMR (300 MHz, CDCl$_3$) δ: 7.930, m, 1H; 7.628, m, 1H; 7.460, m, 1H; 7.233, m, 2H; 7.020, m, 2H; 5.625, m, 1H; 4.728, m, 1H; 3.692, m, 1H; 2.415-1.211, m, 10H; 0.936, s, 9H; −0.100, s, 6H.

LCMS m/z=684.00/685.96 M+H.

Step 6: [5-(tert-Butyl-dimethyl-silanyloxymethyl)-1-cyclohexyl-1H-benzoimidazol-2-yl]-[5-(4-methoxy-pyridin-3-yl)-1-(2-trimethylsilanyl-ethoxymethyl)-1H-indazol-3-yl]-amine A mixture of 5-bromo-1-(2-trimethylsilanyl-ethoxymethyl)-1H-indazol-3-yl]-[5-(tert-butyl-dimethyl-silanyloxymethyl)-1-cyclohexyl-1H-benzoimidazol-2-yl]-amine (448 mg, 0.000654 mol), 4-methoxypyridin-3-yl-3-boronic acid (188 mg, 0.00123 mol), (1,1'-bis(diphenylphosphino) ferrocene)dichloropalladium(II), complexed with dichloromethane (1:1) (83 mg, 0.00010 mol), 1.5 mL 2.0 M sodium carbonate in 1,4-dioxane (6.0 mL) was flushed with argon, sealed, and microwaved at 110° C. for 2 hours. The reaction was diluted with methylene chloride, washed with saturated sodium bicarbonate, dried over magnesium sulfate, filtered, and concentrated to yield the title compound which was used directly in the next step.

Step 7: (1-cyclohexyl-2-(5-(4-methoxypyridin-3-yl)-1H-indazol-3-ylamino)-1H-benzo[d]imidazol-5-yl)methanol A mixture of [5-(tert-Butyl-dimethyl-silanyloxymethyl)-1-cyclohexyl-1H-benzoimidazol-2-yl]-[5-(4-methoxy-pyridin-3-yl)-1-(2-trimethylsilanyl-ethoxymethyl)-1H-indazol-3-yl]-amine (from Step 6) and 12 M HCl (2.0 mL) in ethanol (6.0 mL) was heated at 100° C. for 1 hr. The mixture was evaporated to dryness and then purified twice by preparative HPLC to yield 4.1 mg of the title compound as the TFA salt.

$^1$H NMR (300 MHz, DMSO-d6) δ 8.820-8.642, m, 2H; 8.024, m, 1H; 7.810, m, 1H, 7.723-7.578, m, 3H; 7.471, m, 1H, 7.239, m, 1H; 5.778, m, 1H; 4.738, m, 2H; 4.096, m, 4.020, s, 3H; 2.718, m, 1H; 2.718, m, 1H; 2.365-2.165, m, 2H; 2.079-1.841, m, 3H; 1.767-1.618, m, 1H; 1.575-1.348, m, 3H.

LCMS m/z=469.00 M+H.

Example 17

4-{5-Hydroxymethyl-2-[5-(4-methoxy-pyridin-3-yl)-1H-indazol-3-ylamino]-benzoimidazol-1-yl}-cyclohexanol

Step 1: 4-trans-(4-(hydroxymethyl)-2-nitrophenylamino)cyclohexanol

A mixture of (4-fluoro-3-nitrophenyl)methanol (2.00 g, 0.0117 mol), N,N-diisopropylethylamine (4.07 mL, 0.0234 mol), and trans-4-aminocyclohexanol (2.02 g, 0.018 mol) in N,N-dimethylformamide (4.92 mL) was divided equally among 4 microwave vials and the contents mixed throughly. The mixtures were microwaved at 130° C. for 7 min. The gelationous product was dissolved in ethyl acetate, washed with with 5% citric acid, saturated bicarbonate, brine, dried over magnesium sulfate and concentrated to give the title compound which was used directly in the next step.

MS (ESI (+)m/z): 266.75 (M+H+).

Step 2: 4-trans-(2-amino-4-(hydroxymethyl)phenylamino)cyclohexanol

To 4-(trans-4-(hydroxymethyl)-2-nitrophenylamino)cyclohexanol (2.98 g, 0.0112 mol) in ethanol (100 mL) was added 5% Pd/C (0.50 g, 0.0002 mol). The mixture was flushed with hydrogen then stirred at ambient temperature under hydrogen for 2 hr. The reaction was concentrated and the residue purified by flash chromatography using a 10% methanol in methylene chloride. The product fractions were concentrated to give 1.59 g of the title compound.

MS (ESI (+)m/z): 236.23 (M+H+).

Step 3: 4-trans-(2-amino-5-(hydroxymethyl)-1H-benzo[d]imidazol-1-yl)cyclohexanol A solution of 4-trans-(2-amino4-(hydroxymethyl)phenylamino)cyclohexanol (1.59 g, 0.00673 mol) in methanol (200 mL, 4 mol) was added dropwise over 1 hr to a mixture of 5 M cyanogen bromide in acetonitrile (2.0 mL) and water (70 mL). The reaction was stirred for 3 hr then concentrated. The residue was purified by preparative HPLC using a 2 to 35% gradient over 20 min. Concentration of the product fractions gave 1.38 grams of the title compound—TFA salt as a white powder.

MS (ESI (+)m/z): 261.69 (M+H+).

Step 4: 1-(4-trans-(tert-butyldimethylsilyloxy)cyclohexyl)-5-((tert-butyldimethylsilyloxy)methyl)-1H-benzo[d]imidazol-2-amine tert-Butyldimethylsilyl chloride (1.0 g, 0.0069 mol) was added to a mixture of 4-trans-(2-amino-5-(hydroxymethyl)-1H-benzo[d]imidazol-1-yl)cyclohexanol (0.855 g, 0.00327 mol) and imidazole (0.74 g, 0.011 mol) in N,N-dimethylformamide (10 mL) and the mixture was allowed to stir for 1 hr. The mixture was diluted with ethyl acetate, washed with saturated sodium bicarbonate, brine, dried over magnesium sulfate and concentrated. The residue was dissolved in methylene chloride containing 0.1% triethylamine and purified by flash chromatography with a gradient of 0 to 10 percent methanol. The product fractions were concentrated to give 1.7 g of the title compound.

MS (ESI (+) m/z): 490.14 (M+H+).

Step 5: 5-bromo-N-(1-(4-trans-(tert-butyldimethylsilyloxy)cyclohexyl)-5-((tert-butyldimethylsilyloxy)methyl)-1H-benzo[d]imidazol-2-yl)-1-((2-(trimethylsilyl)ethoxy)methyl)-1H-indazol-3-amine A mixture of 1-(4-trans-(tert-butyldimethylsilyloxy)cyclohexyl)-5-((tert-butyldimethylsilyloxy)methyl)-1H-benzo[d]imidazol-2-amine (850 mg, 0.0017 mol), 5-bromo-3-iodo-1-((2-(trimethylsilyl)ethoxy)methyl)-1H-indazole (1200 mg, 0.0028 mol), xantphos (248 mg, 0.000429 mol), tris(dibenzylideneacetone)dipalladium(0) (194 mg, 0.000212 mol), and potassium phosphate (760 mg, 0.00358 mol) in 1,4-dioxane (8.8 mL) was microwaved at 300 watts, 130° C. for 15 minutes. The mixture was diluted with ethyl acetate, washed with saturated bicarbonate, brine, dried over magnesium sulfate and concentrated. The residual oil was dissolved in methylene chloride and chromatographed by flash chromatography to yield 700 mg of the title compound.

MS (ESI (+) m/z): 815.89 (M+H+).

Step 6: [1-[4-(tert-Butyl-dimethyl-silanyloxy)-cyclohexyl]-5-(tert-butyl-dimethyl-silanyloxymethyl)-1H-benzoimidazol-2-yl]-[5-(4-methoxy-pyridin-3-yl)-1-(2-trimethylsilanyl-ethoxymethyl)-1H-indazol-3-yl]-amine A mixture of 5-bromo-N-(1-(4-trans-(tert-butyldimethylsilyloxy)cyclohexyl)-5-((tert-butyldimethylsilyloxy)methyl)-1H-benzo[d]imidazol-2-yl)-1-((2-(trimethylsilyl)ethoxy)methyl)-1H-indazol-3-amine (505 mg, 0.000620 mol), 4-methoxypyridin-3-yl-3-boronic acid (133 mg, 0.000870 mol) and (1,1'-Bis(diphenylphosphino)ferrocene)dichloropalladium(II), complexed with dichloromethane (1:1) (80 mg, 0.000098 mol) was dissolved in 1,4-dioxane (8.0 mL). To this solution was added 2.0 M sodium carbonate in water (2.0 mL) with stirring. The mixture was flushed with argon, sealed then heated at 110° C. for 1.5 hours. The mixture was then diluted with methylene chloride, washed with water, saturated sodium bicarbonate, dried over magnesium sulfate and concentrated. The residue was purified by flash chromatography to yield 165 mg of the title compound.

MS (ESI (+) m/z): 843.12 (M+H+).

Step 7: 4-(5-(hydroxymethyl)-2-(5-(4-methoxypyridin-3-yl)-1H-indazol-3-ylamino)-1H-benzo[d]imidazol-1-yl)cyclohexanol (1-(4-(tert-Butyl-dimethyl-silanyloxy)-cyclohexyl)-5-(tert-butyl-dimethyl-silanyloxymethyl)-1H-benzoimidazol-2-yl)-(5-(4-methoxy-pyridin-3-yl)-1-(2-trimethylsilanyl-ethoxymethyl)-1H-indazol-3-yl)-amine (165 mg, 0.000196 mol) was dissolved in ethanol (6.0 mL). To this solution was added 12 M HCl (2.0 mL) and the reaction was stirred at 100° C. for 1.5 hours. The reaction was evaporated to dryness and the residue was purified by preparative HPLC to yield 17.1 mg of the title compound as the TFA salt.

$^1$H NMR (300 MHz, DMSO-d6) δ 13.212, s (br), 1H; 8.783, m, 1H; 8.692, s, 1H; 8.065, s, 1H; 7.773, m, 1H; 7.717-7.584, m, 3H; 7.478, s, 1H; 7.224, m, 1H; 4.761, m, 1H; 4.555, s, 2H; 4.040, s, 3H; 3.723, m, 1H; 2.422-2.287, m, 2H; 2.068-1.898, m, 4H; 1.517-1.351, m, 2H.

MS (ESI (+) m/z): 485.07 (M+H+).

The ability of compounds of formula (I) to modulate the activity of IRAK proteins can be assessed by the method described in the following example.

Example 18

IRAK4 TR-FRET Assay

Materials

Biotinylated IRAK1 peptide (IRAK1 AA358-389, GLARFSRFAGSSPSQSSMVARTQTVRGTLA [SEQ ID NO: 1], N-terminus:Biotin, C-terminus:Amide) was synthesized by Advanced ChemTech (Louisville, Ky.), Streptavidin Allophycocyanin (SA-APC) was obtained from ProZyme (San Leandro, Calif.), Polyclonal AntiphosphoThreonine antibody was obtained from Cell Signaling Technologies, Inc. (Danvers, Mass.), LANCE Eu-W1024 Anti Rabbit IgG and LANCE 10× detection buffer were obtained from Perkin Elmer (Wellesley, Mass.), SuperBlok in TBS was obtained from Pierce (Rockford, Ill.), ATP was purchased from Invitrogen (Carlsbad, Calif.) and DMSO was obtained from Fisher Scientific (Fairlawn N.J.).

The IRAK 4 Construct CH373 was synthesized at Biogen Idec. Its amino acid sequence is

[SEQ ID NO: 2]
MSYYHHHHHHDYDIPTTENLYFQGAMGDRTLMTPVQNLEQSYMPPDSSSPENKSLE

VSDTRFHSFSFYELKNVTNNFDERPISVGGNKMGEGGFGVVYKGYVNNTTVAVKKL

AAMVDITTEELKQQFDQEIKVMAKCQHENLVELLGFSSDGDDLCLVYVYMPNGSLL

DRLSCLDGTPPLSWHMRCKIAQGAANGINFLHENHHIHRDIKSANILLDEAFTAKISD

FGLARASEKFAQTVMTSRIVGTTAYMAPEALRGEITPKSDIYSFGVVLLEIITGLPAVD

-continued

EHREPQLLLDIKEEIEDEEKTIEDYIDKKMNDADSTSVEAMYSVASQCLHEKKNKRP

DIKKVQQLLQEMTAS.

Assay

5 µL of the test compound at a concentration of 50 µM or less in 1% (v/v) DMSO is added to the wells of a 96-well ½ area Black Polystyrene plates (Costar 3694). The final concentrations in the reaction well are 10 µM ATP, 0.5 µM IRAK4 CH373, 1.6 µM IRAK1 peptide, 1% DMSO, 50 mM HEPES, 60 mM NaCl, 1 mM MgCl2, 2 mM DTT, 5 mM MnCl2, 0.01% BSA, 0.01% Tween-20. The volume of the reaction is 45 µL. The reaction is incubated at room temperature for 30 minutes and stopped with the addition of 5 µL of 100 mM EDTA.

Detection: 25 µL of a solution containing 160 ηM SA-APC, 1×LANCE detection buffer and 1% Superblock in TBS and 25 µL of a solution containing 100 ηM Polyclonal Anti p-Thr, 20 ηM Eu-Anti Rabbit IgG, 1× LANCE detection buffer and 1% Superblock in TBS are added to each well. The plates are covered with a foil lid and incubated for at least 30 minutes at room temperature. The plates are read on an Analyst AD, LJL BioSystems, ID1615. The recommended settings are: Type: MultiMethod; Name: HTRF-EuK; Plate format: LJL HE 96 A Black PS; Z height: 2 mm; Raw units: counts; Ratio: acceptor/donor, Acceptor: HRTF(Packard) acceptor: Excitation: Europium FRET 330 ηm, Emission: FRET acceptor 665 ηm, Donor: HRTF(Packard) donor: Excitation: Europium FRET 330 ηm, Emission: FRET chelate donor; Flashes/well: 100; Intergration time: 400 µs; Interval between: 1×10 ms flashes; Delay after flash: 50 µs. Control wells measuring total signal contained 1% (v/v) DMSO only (no test compound). Control wells measuring background signal contained 1% (v/v) DMSO/50 mM EDTA.

Compounds of formula (I) typically exhibited $IC_{50}$ values of less than 20 µM; some of the compounds exhibited $IC_{50}$ values of less than 1 µM; and some had $IC_{50}$ values of less than 10 nM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A compound of Formula (I)

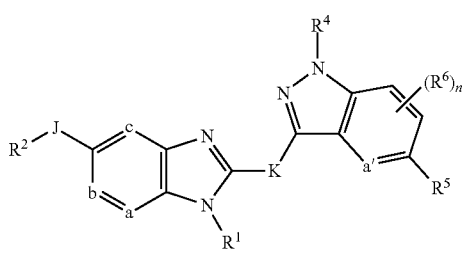

(I)

wherein:

$R^1$ is an optionally substituted aliphatic, an optionally substituted cycloaliphatic, an optionally substituted heterocycloaliphatic, an optionally substituted aryl, or an optionally substituted heteroaryl;

$R^2$ is H, an optionally substituted aliphatic, an optionally substituted cycloaliphatic, an optionally substituted heterocycloaliphatic, an optionally substituted aryl, or an optionally substituted heteroaryl;

each of a, a', b, and c is independently N or C($R^3$);

each of $R^3$, $R^5$, and $R^6$ is independently H, an optionally substituted aliphatic, an optionally substituted alkoxy, acyl, halo, hydroxy, amino, nitro, cyano, guanadino, amidino, carboxy, sulfo, mercapto, sulfanyl, sulfinyl, sulfonyl, sulfonamide, amido, sulfamide, urea, thiourea, carbamoyl, cycloaliphatic, cycloalkyloxy, heterocycloaliphatic, heterocycloalkyloxy, aryl, aralkyl, aryloxy, aroyl, heteroaryl, heteroaralkyl, heteroaryloxy, or heteroaroyl;

$R^4$ is H;

K is —N($R^{X'}$)—;

J is a bond, —O—, —S(O)$_i$—, —N($R^{X'}$)—, alkylene, —C(O)—, —C(O)—O—, —C(O)—N($R^{X'}$)—, —(CH$_2$)$_p$N($R^{X'}$)—, or —N($R^{X'}$)—C(O)—;

$R^{X'}$ is independently H or an optionally substituted aliphatic;

n is 0, 1, 2, or 3;

i is 0, 1, or 2;

p is 1, 2, 3, or 4; and provided that when $R^1$ is an unsubstituted alkyl and J is —O—, then $R^2$ is H, an optionally substituted aliphatic, an optionally substituted aryl, or an unsubstituted heteroaryl.

2. The compound of claim 1, wherein $R^{X'}$ is H.

3. The compound of claim 1, wherein $R^1$ is an optionally substituted aliphatic, or an optionally substituted cycloaliphatic.

4. The compound of claim 3, wherein $R^1$ is alkyl optionally substituted with halo, amino, amido, hydroxyl, or alkoxy; or $R^1$ is a cycloalkyl optionally substituted with: hydroxyl, halo, amido, amino, alkoxy, cyano, carboxy, optionally substituted aliphatic, optionally substituted cycloaliphatic, or optionally substituted heterocycloaliphatic.

5. The compound of claim 4, wherein $R^1$ is an optionally substituted bicycloaliphatic.

6. The compound of claim 1, wherein $R^1$ is an optionally substituted heterocycloaliphatic, an optionally substituted aryl, or an optionally substituted heteroaryl.

7. The compound of claim 1, wherein J is a bond, —O—, —N($R^{X'}$)—, alkylene, —C(O)—, —C(O)—O—, —C(O)—N($R^{X'}$)—, —(CH$_2$)$_p$—N($R^{X'}$)—, or —N($R^{X'}$)—C(O)—.

8. The compound of claim 7, wherein J is —C(O)—, —CH$_2$—, a bond, or an alkylene.

9. The compound of claim 1, wherein $R^2$-J- is H, HO—CH$_2$—, ((((pyridin-4-yl)ethyl)piperazin-1-yl)methyl)-, CH$_3$CH$_2$O—C(O)—, morpholinomethyl, cyclopentylaminocarbonyl, isopentylaminocarbonyl, piperidinylmethyl, or pyrolidinecarbonyl.

10. The compound of claim 1, wherein $R^5$ is an optionally substituted aryl or an optionally substituted heteroaryl.

11. The compound of claim 10, wherein $R^5$ is a heteroaryl optionally substituted with 1 to 3 alkyl, alkoxy, amino, carboxy, amido, halo or cyano; or $R^5$ is an aryl optionally substituted with alkyl, alkoxy, amino, halo, or cyano.

12. The compound of claim 11, wherein $R^5$ is pyridyl optionally substituted with alkyl, alkoxy, amino, amido, halo, or cyano; or $R^5$ is phenyl optionally substituted with alkyl, alkoxy, amino, halo, or cyano.

13. The compound of claim 12, wherein $R^5$ is (4-methoxy)pyridin-3-yl, 3-methoxymethylphenyl, 2-methoxyphenyl, or 2-trifluoromethoxyphenyl.

14. The compound of claim 1, wherein $R^5$ is bromo, H, or phenyl substituted with —N($R^{X'}$)($R^{Y'}$), —N($R^{X'}$)—C(O)—$R^{Y'}$, or —N($R^{X'}$)—S(O)$_2$—$R^{Y'}$, wherein $R^{Y'}$ is independently H or an optionally substituted aliphatic.

15. The compound of claim 14, wherein $R^5$ is 3-aminophenyl.

16. The compound of claim 1, wherein n is 0 or n is 1.

17. The compound of claim 1, wherein each of a, a', b, and c is independently CR$^3$.

18. The compound of claim 17, wherein $R^3$ is H.

19. The compound of claim 1, wherein one or two of a, a', b, and c are N.

20. The compound of claim 1, wherein $R^1$ is a cycloaliphatic optionally substituted with hydroxy; J is —CH$_2$—, —C(O)—, or —CH$_2$—N($R^{X'}$)—; $R^5$ is optionally substituted phenyl or pyridyl; each of a, a', b, and c is independently CH; and n is 0.

21. The compound of claim 20, wherein J is —CH$_2$—; and $R^2$ is an optionally substituted heterocycle containing at least one N attached to J.

22. The compound of claim 1, wherein $R^1$ is aliphatic optionally substituted with hydroxy; $R^2$J- is H; $R^5$ is H or halo; each of a, a', b, and c is independently CH; and n is 0.

23. The compound of claim 1, wherein K is —NH—; $R^1$ is an alkyl or cyclohexyl, optionally substituted with hydroxy; J is a bond or —CH$_2$—; $R^2$ is alkyl, cycloalkyl, or heterocycloalkyl; $R^5$ is heteroaryl or amino phenyl; and n is 0.

24. The compound of claim 1, wherein the compound is:
(2-(5-(3-aminophenyl)-1H-indazol-3-ylamino)-1-cyclohexyl-1H-benzo[d]imidazol-6-yl)methanol;
(1-cyclohexyl-2-(5-(3-(methoxymethyl)phenyl)-1H-indazol-3-ylamino)-1H-benzo[d]imidazol-5-yl)methanol;
4-(2-(5-(4-methoxypyridin-3-yl)-1H-indazol-3-ylamino)-5((4-(2-(pyridin-4-yl)ethyl)piperazin-1-yl)methyl)-1H-benzo[d]imidazol-1-yl)cyclohexanol;
ethyl 1-((2-(5-(4-methoxypyridin-3-yl)-1H-indazol-3-ylamino)-1-(4-hydroxycyclohexyl)-1H-benzo[d]imidazol-5-yl)methyl)piperidine-4-carboxylate;
(2-(5-(4-methoxypyridin-3-yl)-1H-indazol-3-ylamino)-1-phenyl-1H-benzo[d]imidazol-5-yl)methanol;
N-(1-cyclohexyl-5-(morpholinomethyl)-1H-benzo[d]imidazol-2-yl)-5-(4-methoxypyridin-3-yl)-1H-indazol-3-amine;
2-(5-(2-methoxyphenyl)-1H-indazol-3-ylamino)-N-cyclopentyl-1-(4-hydroxycyclohexyl)-1H-benzo[d]imidazole-5-carboxamide;
1-(4-hydroxycyclohexyl)-N-isopentyl-2-(5-(2-methoxyphenyl)-1H-indazol-3-ylamino)-1H-benzo[d]imidazole-5-carboxamide;
(1-(4-hydroxycyclohexyl)-2-(5-(2-methoxyphenyl)-1H-indazol-3-ylamino)-1H-benzo[d]imidazol-5-yl)(pyrolidin-1-yl)methanone;
N-cyclopentyl-1-(4-hydroxycyclohexyl)-2-(5-(2-(trifluoromethoxy)phenyl)-1H-indazol-3-ylamino)-1H-benzo[d]imidazole-5-carboxamide;
2-(5-(2-(trifluoromethoxy)phenyl)-1H-indazol-3-ylamino)-1-(4-hydroxycyclohexyl)-N-isopentyl-1H-benzo[d]imidazole-5-carboxamide;
ethyl 1-(4-hydroxycyclohexyl)-2-(5-(4-methoxypyridin-3-yl)-1H-indazol-3-ylamino)-1H-benzo[d]imidazole-5-carboxylate;
4-(5-(hydroxymethyl)-2-(5-(4-methoxypyridin-3-yl)-1H-indazol-3-ylamino)-1H-benzo[d]imidazol-1-yl)cyclohexanol;
(1-cyclohexyl-2-(5-(4-methoxypyridin-3-yl)-1H-indazol-3-ylamino)-1H-benzo[d]imidazol-5-yl)methanol;
N-(1-cyclohexyl-5-(piperidin-1-ylmethyl)-1H-benzo[d]imidazol-2-yl)-5-(4-methoxypyridin-3-yl)-1H-indazol-3-amine;
3-(2-(5-(4-methoxypyridin-3-yl)-1H-indazol-3-ylamino)-1H-benzo[d]imidazol-1-yl)propan-1-ol; or
3-(2-(5-bromo-1H-indazol-3-ylamino)-1H-benzo[d]imidazol-1-yl)propan-1-ol.

25. A pharmaceutical composition comprising a pharmaceutically acceptable carrier or excipient and a compound of claim 1.

26. A method of treating rheumatoid arthritis or osteoarthritis in a subject, comprising administering to the subject in need of such treatment a therapeutically effective amount of a compound of claim 1.

27. The method of claim 26, wherein said compound is administered in combination with a therapeutic agent selected from the group consisting of methotrexate, sulfasalazine, a COX-2 inhibitor, hydroxychloroquine, cyclosporine A, D-penicillamine, infliximab, etanercept, auranofin, aurothioglucose, sulfasalazine, sulfasalazine analogs, mesalamine, corticosteroids, corticosteroid analogs, 6-mercaptopurine, cyclosporine A, methotrextate and infliximab, interferon beta-1 beta, interferon beta-1 alpha, azathioprine, glatiramer acetate, a glucocorticoid, and cyclophosphamide.

* * * * *

SEQUENCE LISTING

```
<160> NUMBER OF SEQ ID NOS: 2

<210> SEQ ID NO 1
<211> LENGTH: 30
<212> TYPE: PRT
<213> ORGANISM: Artificial
<220> FEATURE:
<223> OTHER INFORMATION: Synthetically Generated Sequence
<220> FEATURE:
<221> NAME/KEY: PEPTIDE
<222> LOCATION: (1)..(29)
<220> FEATURE:
<221> NAME/KEY: PEPTIDE
<222> LOCATION: (1)..(30)

<400> SEQUENCE: 1

Gly Leu Ala Arg Phe Ser Arg Phe Ala Gly Ser Ser Pro Ser Gln Ser
1               5                   10                  15

Ser Met Val Ala Arg Thr Gln Thr Val Arg Gly Thr Leu Ala
            20                  25                  30

<210> SEQ ID NO 2
<211> LENGTH: 357
<212> TYPE: PRT
<213> ORGANISM: Homo sapiens

<400> SEQUENCE: 2

Met Ser Tyr Tyr His His His His His Asp Tyr Asp Ile Pro Thr
1               5                   10                  15

Thr Glu Asn Leu Tyr Phe Gln Gly Ala Met Gly Asp Arg Thr Leu Met
            20                  25                  30

Thr Pro Val Gln Asn Leu Glu Gln Ser Tyr Met Pro Pro Asp Ser Ser
        35                  40                  45

Ser Pro Glu Asn Lys Ser Leu Glu Val Ser Asp Thr Arg Phe His Ser
    50                  55                  60
```

```
Phe Ser Phe Tyr Glu Leu Lys Asn Val Thr Asn Asn Phe Asp Glu Arg
 65              70                  75                  80

Pro Ile Ser Val Gly Gly Asn Lys Met Gly Glu Gly Phe Gly Val
             85                  90                  95

Val Tyr Lys Gly Tyr Val Asn Asn Thr Thr Val Ala Val Lys Lys Leu
            100                 105                 110

Ala Ala Met Val Asp Ile Thr Thr Glu Glu Leu Lys Gln Gln Phe Asp
            115                 120                 125

Gln Glu Ile Lys Val Met Ala Lys Cys Gln His Glu Asn Leu Val Glu
        130                 135                 140

Leu Leu Gly Phe Ser Ser Asp Gly Asp Asp Leu Cys Leu Val Tyr Val
145                 150                 155                 160

Tyr Met Pro Asn Gly Ser Leu Leu Asp Arg Leu Ser Cys Leu Asp Gly
                165                 170                 175

Thr Pro Pro Leu Ser Trp His Met Arg Cys Lys Ile Ala Gln Gly Ala
                180                 185                 190

Ala Asn Gly Ile Asn Phe Leu His Glu Asn His His Ile His Arg Asp
            195                 200                 205

Ile Lys Ser Ala Asn Ile Leu Leu Asp Glu Ala Phe Thr Ala Lys Ile
    210                 215                 220

Ser Asp Phe Gly Leu Ala Arg Ala Ser Glu Lys Phe Ala Gln Thr Val
225                 230                 235                 240

Met Thr Ser Arg Ile Val Gly Thr Thr Ala Tyr Met Ala Pro Glu Ala
            245                 250                 255

Leu Arg Gly Glu Ile Thr Pro Lys Ser Asp Ile Tyr Ser Phe Gly Val
            260                 265                 270

Val Leu Leu Glu Ile Ile Thr Gly Leu Pro Ala Val Asp Glu His Arg
        275                 280                 285

Glu Pro Gln Leu Leu Leu Asp Ile Lys Glu Glu Ile Glu Asp Glu Glu
    290                 295                 300

Lys Thr Ile Glu Asp Tyr Ile Asp Lys Lys Met Asn Asp Ala Asp Ser
305                 310                 315                 320

Thr Ser Val Glu Ala Met Tyr Ser Val Ala Ser Gln Cys Leu His Glu
            325                 330                 335

Lys Lys Asn Lys Arg Pro Asp Ile Lys Lys Val Gln Gln Leu Leu Gln
            340                 345                 350

Glu Met Thr Ala Ser
            355
```